United States Patent [19]

Tseng

[11] Patent Number: 5,631,210
[45] Date of Patent: May 20, 1997

[54] HERBICIDAL THIOPHENE KETONES

[75] Inventor: Chi-Ping Tseng, Wilmington, Del.

[73] Assignee: E. I. Du Pont de Nemours and Company, Wilmington, Del.

[21] Appl. No.: 665,166

[22] Filed: Jun. 14, 1996

[51] Int. Cl.$^6$ .................. A01N 43/56; A01N 43/18; C07D 231/18; C07D 409/02
[52] U.S. Cl. .................. 504/282; 504/288; 548/364.4; 549/9; 549/12; 549/23; 549/26; 549/27
[58] Field of Search .................. 548/374.1, 364.4; 549/9, 12, 23, 16, 26, 27; 504/288, 290, 282, 280; 514/431, 432, 404, 407, 406

[56] References Cited

U.S. PATENT DOCUMENTS

| | | | |
|---|---|---|---|
| 3,487,085 | 12/1969 | Protiva et al. | 549/23 |
| 3,591,605 | 7/1971 | Mizutani et al. | 549/23 |
| 3,636,041 | 1/1972 | Schmidt et al. | 549/23 |
| 4,134,900 | 1/1979 | Sicar et al. | 549/23 |
| 4,730,054 | 3/1988 | Leiner et al. | 548/336 |
| 4,772,309 | 9/1988 | Stetter et al. | 504/282 |
| 5,380,748 | 1/1995 | Mato et al. | 514/434 |
| 5,468,722 | 11/1995 | Shibata et al. | 504/282 |

FOREIGN PATENT DOCUMENTS

| | | |
|---|---|---|
| 283261 | 8/1994 | European Pat. Off. |
| 03120202A2 | 5/1991 | Japan. |
| WO95/04054 | 2/1995 | WIPO. |

*Primary Examiner*—José G. Dees
*Assistant Examiner*—Deborah Lambkin

[57] ABSTRACT

Compounds of Formula I and their agriculturally suitable salts are disclosed which are useful for controlling undesired vegetation

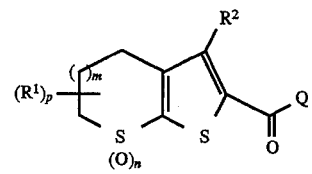

wherein
Q is

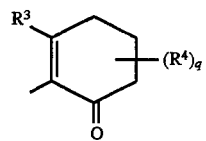

or

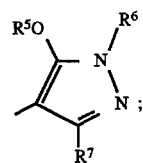

and $R^1$ through $R^7$, m, n, p and q are as defined in the disclosure.

Also disclosed are compositions containing the compounds of Formula I and a method for controlling undesired vegetation which involves contacting the vegetation or its environment with an effective amount of a compound of Formula I.

6 Claims, No Drawings

HERBICIDAL THIOPHENE KETONES

BACKGROUND OF THE INVENTION

This invention relates to certain thiophene ketones, their agriculturally suitable salts and compositions, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action.

EP 283,261 discloses heterocycles of Formula i as herbicides:

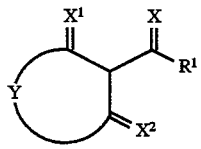

wherein

X, $X^1$ and $X^2$ are independently O or S;

$R^1$ is a monocyclic or fused-bicyclic heterocyclic group optionally substituted by one or more groups selected from oxo, mercapto, halo, nitro, cyano, amino, mono- or dialkylamino, amido, alkyl, alkenyl, alkynyl, cycloalkyl, haloalkyl, haloalkoxy, aryl, hydroxy, alkoxy, alkoxycarbonyl, alkylcarbonyl, mono- or dialkylcarbamoyl, alkylthio, alkylsulfinyl, alkylsulfonyl, sulfonamido, alkylcarbonyloxy, alkylcarbonylamino or heterocyclyl; and Y is, inter alia, $C_2$-$C_4$ alkylene.

The thiophene ketones of the present invention are not disclosed therein.

SUMMARY OF THE INVENTION

This invention is directed to compounds of Formula I including all geometric and stereoisomers, agriculturally suitable salts thereof, agricultural compositions containing them and their use for controlling undesirable vegetation:

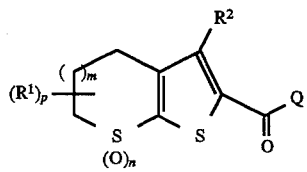

wherein

Q is

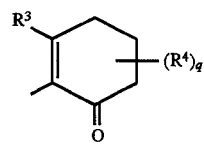

or

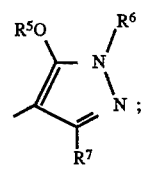

each $R^1$ is independently $C_1$-$C_6$ alkyl, $C_1$-$C_6$ haloalkyl, $C_1$-$C_6$ alkoxy, $C_1$-$C_6$ haloalkoxy, hydroxy, or halogen; or two $R^1$ bonded to the same carbon atom can be taken together with the carbon to which they are attached to form C(=O) or C(=N—$OR^8$); or two $R^1$ bonded to the same carbon atom can be taken together as —$OCH_2CH_2O$— or —$OCH_2CH_2CH_2O$—, each optionally substituted with 1-2 $C_1$-$C_3$ alkyl or 1-4 halogen;

$R^2$ is H, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, halogen, cyano or nitro;

$R^3$ is $OR^9$, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or halogen;

each $R^4$ is independently $C_1$-$C_3$ alkyl, $C_1$-$C_3$ alkoxy, $C_1$-$C_3$ alkylthio or halogen; or when two $R^4$ are attached to the same carbon atom, then said $R^4$ pair can be taken together to form —$OCH_2CH_2O$—, —$OCH_2CH_2CH_2O$—, —$SCH_2CH_2S$— or —$SCH_2CH_2CH_2S$—, each group optionally substituted with 1-4 $CH_3$;

$R^5$ is H, $C_1$-$C_6$ alkyl, $C_1$-$C_6$ haloalkyl, $C_2$-$C_6$ alkoxyalkyl, formyl, $C_2$-$C_6$ alkylcarbonyl, $C_2$-$C_6$ alkoxycarbonyl, $C_2$-$C_6$ alkylaminocarbonyl, $C_3$-$C_7$ dialkylaminocarbonyl, $C_1$-$C_6$ alkylsulfonyl or $C_1$-$C_6$ haloalkylsulfonyl; or $R^5$ is benzoyl or phenylsulfonyl, each optionally substituted with $C_1$-$C_3$ alkyl, halogen, cyano or nitro;

$R^6$ is H, $C_1$-$C_6$ alkyl, $C_1$-$C_6$ haloalkyl, $C_3$-$C_6$ alkenyl or $C_3$-$C_6$ alkynyl; or $R^6$ is phenyl or benzyl, each optionally substituted on the phenyl ring with $C_1$-$C_3$ alkyl, halogen, cyano or nitro;

$R^7$ is H, $C_1$-$C_6$ alkyl, $C_1$-$C_6$ haloalkyl, halogen, cyano or nitro;

$R^8$ is H, $C_1$-$C_6$ alkyl, $C_1$-$C_6$ haloalkyl, $C_3$-$C_6$ alkenyl or $C_3$-$C_6$ alkynyl;

$R^9$ is H, $C_1$-$C_6$ alkyl, $C_1$-$C_6$ haloalkyl, C2-$C_6$ alkoxyalkyl, formyl, $C_2$-$C_6$ alkylcarbonyl, $C_2$-$C_6$ alkoxycarbonyl, $C_2$-$C_6$ alkylaminocarbonyl, $C_3$-$C_7$ dialkylaminocarbonyl, $C_1$-$C_6$ alkylsulfonyl or $C_1$-$C_6$ haloalkylsulfonyl; or $R^9$ is benzoyl or phenylsulfonyl, each optionally substituted with $C_1$-$C_3$ alkyl, halogen, cyano or nitro;

m is 1 or 2;

n is 0, 1 or 2; and p and q are each independently 0, 1, 2, 3 or 4;

provided that, when Q is Q-1, then n is 1 or 2.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 alkyl" indicates that one or two of the available positions for that substituent may be alkyl. "Alkenyl" includes straight-chain or branched alkenes such as 1-propenyl, 2-propenyl, and the different butenyl, pentenyl and hexenyl isomers. "Alkenyl" also includes polyenes such as 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. For example, $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "dialkylamino", and the like, are defined analogously to the above examples.

The term "halogen", either alone or in compound words such as "haloalkyl", includes fluorine, chlorine, bromine or iodine. The term "1–4 halogen" indicates that one to four of the available positions for that substituent may be halogen. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkoxy", "haloalkylthio", "haloalkylsulfonyl", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfonyl" include $CF_3S(O)_2$, $CCl_3S(O)_2$, $CF_3CH_2S(O)_2$ and $CF_3CF_2S(O)_2$.

The total number of carbon atoms in a substituent group is indicated by the "$C_i$–$C_j$" prefix where i and j are numbers from 1 to 7. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers.

When a compound is substituted with a substituent bearing a subscript that indicates the number of said substituents can exceed 1, said substituents (when they exceed 1 ) are independently selected from the group of defined substituents.

When a group contains a substituent which can be hydrogen, for example $R^2$ or $R^6$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate and/or to selectively prepare said stereoisomers. Accordingly, the present invention comprises compounds selected from Formula I and agriculturally suitable salts thereof. The compounds of the invention may be present as a mixture of stereoisomers, individual stereoisomers, or as an optically active form.

Some compounds of this invention can exist as one or more tautomers. One skilled in the art will recognize, for example, that compounds of Formula Ia (Formula I where Q is Q-1, $R^3$ is $OR^9$, and $R^9$ is H) can also exist as the tautomers of Formulae Ib and Ic as shown below. One skilled in the art will recognize that said tautomers often exist in equilibrium with each other. As these tautomers interconvert under environmental and physiological conditions, they provide the same useful biological effects. The present invention includes mixtures of such tautomers as well as the individual tautomers of compounds of Formula I.

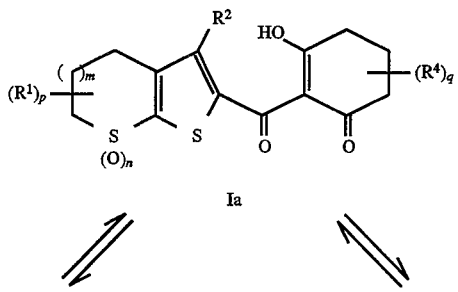

Ia

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as an enol.

Preferred compounds for reasons of better activity and/or ease of synthesis are:

Preferred 1. Compounds of Formula I above, and agriculturally-suitable salts thereof, wherein:
  $R^2$ is $C_1$–$C_3$ alkyl or halogen;
  $R^4$ is $C_1$–$C_3$ alkyl;
  $R^6$ is H, $C_1$–$C_6$ alkyl or $C_2$–$C_6$ alkenyl;
  $R^7$ is H;
  $R^9$ is H, formyl, $C_2$–$C_6$ alkylcarbonyl, $C_2$–$C_6$ alkoxycarbonyl, $C_2$–$C_6$ alkylaminocarbonyl, $C_3$–$C_7$ dialkylaminocarbonyl, $C_1$–$C_6$ alkylsulfonyl or $C_1$–$C_6$ haloalkylsulfonyl; or $R^9$ is benzoyl or phenylsulfonyl, each optionally substituted with $C_1$–$C_3$ alkyl, halogen, cyano or nitro; and
  n is 2.

Preferred 2. Compounds of Preferred 1 wherein:
  each $R^1$ is independently $C_1$–$C_3$ alkyl, $C_1$–$C_3$ alkoxy or halogen; or two $R^1$ bonded to the same carbon atom can be taken together with the carbon to which they are attached to form C(=O) or C(=N—$OR^8$); or two $R^1$ bonded to the same carbon atom can be taken together as —$OCH_2CH_2O$— or —$OCH_2CH_2CH_2O$—, each optionally substituted with 1–2 $C_1$–$C_3$ alkyl or 1–4 halogen;
  $R^2$ is methyl or halogen;
  $R^3$ is $OR^9$;
  $R^5$ is H or $C_1$–$C_2$ alkylsulfonyl; or $R^5$ is benzoyl or phenylsulfonyl, each optionally substituted with $C_1$–$C_3$ alkyl, halogen, cyano or nitro;
  $R^8$ is $C_1$–$C_3$ alkyl;
  $R^9$ is H or $C_1$–$C_2$ alkylsulfonyl; or $R^9$ is benzoyl or phenylsulfonyl, each optionally substituted with $C_1$–$C_3$ alkyl, halogen, cyano or nitro; and
  m is 1.

Most preferred are compounds of Preferred 2 selected from the group:
  2-[(5,6-dihydro-3,4,4-trimethyl-4H-thieno[2,3-b]thiopyran-2-yl)carbonyl]-1,3-cyclohexanedione S,S-dioxide;
  (5,6-dihydro-3,4,4-trimethyl-4H-thieno[2,3-b]thiopyran-2-yl)(1-ethyl-5-hydroxy-1H-pyrazol-4-yl)methanone S,S-dioxide;
  2-[(5,6-dihydro-3-methylspiro[1,3-dioxolane-2,4'-[4H]thieno[2,3-b]thiopyran]-2-yl)carbonyl]-1,3-cyclohexanedione S,S-dioxide; and
  (5,6-dihydro-3-methylspiro[1,3-dioxolane-2,4'-[4H]thieno[2,3-b]thiopyran-]2-yl)(1-ethyl-5-hydroxy-1H-pyrazol-4-yl)methanone S,S-dioxide.

This invention also relates to herbicidal compositions comprising herbicidally effective amounts of the compounds of the invention and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of the invention (e.g., as a composition described herein). The preferred methods of use are those involving the above preferred compounds.

DETAILS OF THE INVENTION

The compounds of Formula I can be prepared by one or more of the following methods and variations as described in Schemes 1–18. The definitions of Q, $R^1$ through $R^9$, m, n, p and q in the compounds of Formulae I–XVI below are as defined above in the Summary of the Invention. Compounds of Formulae Ia–Ie are various subsets of the compounds of Formula I, and all substituents for Formulae Ia–Ie are as defined above for Formula I. Compounds of Formula Id and Ie correspond to Formula I compounds wherein Q is Q–1 and Q–2, respectively.

Scheme 1 illustrates the preparation of compounds of Formula Id ($R^3$=$OR^{10}$ and $R^{10}$ is the same as $R^9$ as described in the Summary of the Invention excluding H) whereby a compound of Formula Id ($R^3$=OH) is reacted with a reagent of Formula II in the presence of a base wherein $X^1$ is chlorine, bromine, fluorine, trifluoromethylsulfonyloxy (OTf), or acetyloxy (OAc) and $R^{10}$ is as previously defined. The coupling is carried out by methods known in the art (or by obvious modifications of these methods): for example, see K. Nakamura, et al., WO 95/04054.

Scheme 1

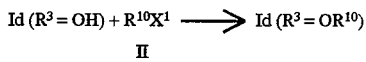

Scheme 2 illustrates the preparation of compounds of Formula Id ($R^3=SO_rR^{11}$; r=1 or 2; and $R^{11}=C_1-C_6$ alkyl or $C_1-C_6$ haloalkyl) whereby a compound of Formula Id ($R^3=SR^{11}$) is reacted with an oxidizing reagent such as peroxyacetic acid, m-chloroperoxybenzoic acid, peroxytrifluoroacetic acid, potassium peroxymonosulfate or hydrogen peroxide. The oxidation is carried out by methods known in the art (or by obvious modifications of these methods); for example, see S. Patai, et al., *The Chemistry of Sulphones and Sulphoxides*, John Wiley & Sons.

Scheme 2

Id ($R^3 = SR^{11}$) + Oxidizing reagent ⟶ Id ($R^3 = S(O)_rR^{11}$)

Compounds of Formula Id ($R^3$=Nu; Nu=$SR^{11}$ or $OR^{12}$; $R^{11}$ is as defined previously; $R^{12}$ is $C_1-C_6$ alkyl, $C_1-C_6$ haloalkyl or $C_2-C_6$ alkoxyalkyl) can be prepared by one skilled in the art from a compound of Formula Id ($R^3$= halogen) by treatment with a nucleophile of Formula III (Nu=$SR^{11}$ or $OR_{12}$; M=Na, K, or Li) as shown in Scheme 3 using methods well documented in the literature (or obvious modifications of these methods): for example, see P. H. Nelson, et al., *Synthesis*, (1992), 12, 1287–1291; and S. Miyano, et al., *J. Chem. Soc. Perkin Trans 1*, (1976), 1146.

Scheme 3

Compounds of Formula Id ($R^3$=halogen) can be prepared by reacting a compound of Formula Id ($R^3$=OH) with a halogenating reagent such as oxalyl bromide or oxalyl chloride (Scheme 4). This conversion is carried out by methods known in the art (or by obvious modifications of these methods): for example, see S. Muller, et al., WO 94/13619; S. Muller, et al., DE 4241999-A1.

Scheme 4

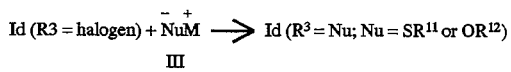

Scheme 5 illustrates the preparation of compounds of Formula Id ($R^3$=OH) whereby an enol ester of Formula IV is reacted with a base such as triethylamine in the presence of a catalytic amount of a cyanide source (e.g., acetone cyanohydrin or potassium cyanide). This rearrangement is carried out by methods known in the art (or by obvious modifications of these methods): for example, see W. J. Michaely, EP 369,803.

Scheme 5

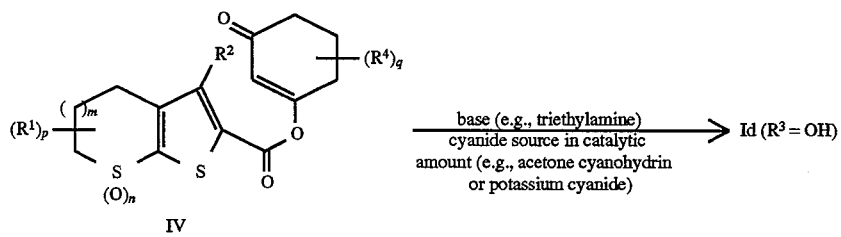

Enol esters of Formula IV can be prepared by reacting a dione of Formula V with an acid chloride of Formula VI in the presence of a slight mole excess of a base such as triethylamine in an inert organic solvent such as acetonitrile, methylene chloride or toluene at temperatures between 0° C. and 110° C. (Scheme 6). This type of coupling is known in the art: for example, see W. J. Michaely, EP 369,803.

Scheme 6

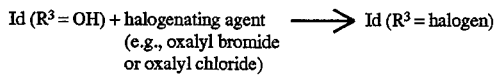

The acid chlorides of Formula VI can be prepared by reacting an acid of Formula VII with a halogenating reagent (e.g., oxalyl chloride or thionyl chloride) and a catalytic amount of dimethylformamide (Scheme 7). This chlorination is well known in the art: for example, see W. J. Michaely, EP 369,803.

Scheme 7

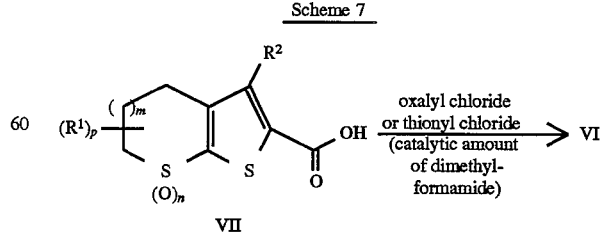

Scheme 8 illustrates the preparation of acids of Formula VII (n=1 or 2) whereby an acid of Formula VII (n=0) is reacted with an oxidizing reagent such as peroxyacetic acid, m-chloroperoxybenzoic acid, peroxytrifluoroacetic acid, potassium peroxymonosulfate, or hydrogen peroxide. The oxidation is carried out by methods known in the art (or by obvious modifications of these methods): for example, see S. Patai, et al., *The chemistry of Sulphones and Sulphoxides*, John Wiley & Sons. For some acids of Formula VII (n=0) containing a functional group not compatible with the reaction conditions, the functional group may be protected before the oxidation and then be deprotected after the oxidation. The protection and deprotection procedures are well known in the literature: for example, see T. W. Greene, et al., *Protective Groups in Organic Synthesis* (Second Edition), John Wiley & Sons, Inc.

Scheme 8

Scheme 9 illustrates the preparation of acids of Formula VII (n=0) whereby a bicyclic thiophene of Formula VIII is treated with a strong base such as n-butyllithium or lithium diisopropylamide (LDA) and the lithium salt generated in situ is then reacted with carbon dioxide followed by acidification with an acid such as hydrochloric acid. This conversion is carried out by methods known in the art (or by obvious modifications of these methods): for example, see S. Gronowitz., *Heterocyclic Compounds* Vol. 44, Part 5, John Wiley and Sons. Compounds containing functional groups not compatible with these reaction conditions may require protection and deprotection procedures.

Scheme 9

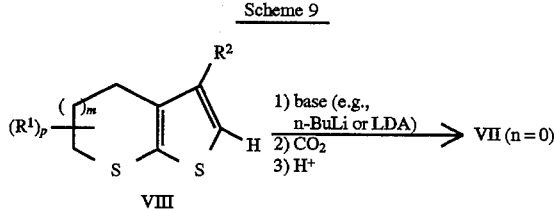

Many bicyclic thiophenes of Formula VIII can be prepared (Scheme 10) by one skilled in the art by modifying the carbonyl functional group of bicyclic thiophenes of Formula VIIIa (p1=0, 1, 2, 3 or 4) using procedures well documented in the literature: for example, see I. T. Harrison, et al., *Compendium of Organic Synthetic Methods*, Vol. 1–7, John Wiley & Sons, Inc.; and T. W. Greene, et al., *Protective Groups in Organic Synthesis* (Second Edition), John Wiley & Sons, Inc. The functional group modifications include but are not limited to the following transformations:

- convening a ketone to an oxime,
- converting a ketone to a cyclic ketal,
- reducing a ketone to an alcohol and then alkylating the alcohol to an alkyl ether,
- reacting a ketone with an alkyl Grignard reagent (or an alkyl lithium reagent) to yield an alcohol and then alkylating the alcohol to an alkyl ether,
- converting a ketone to a halogenated methylene group (through the alcohol intermediate if necessary), and
- reducing a ketone to a methylene group.

Scheme 10

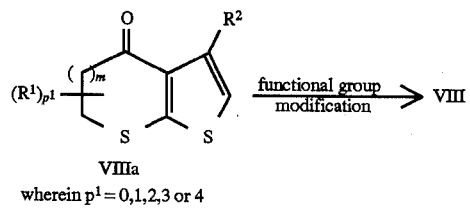

wherein $p^1 = 0,1,2,3$ or 4

Scheme 11 illustrates the preparation of bicyclic thiophenes of Formula VIII ($R^2$ is other than Br) whereby a bicyclic thiophene of Formula VIII ($R^2$=Br) is reacted with n-butyllithium and the lithium salt generated in situ is then reacted with an electrophile (e.g., N,N-dimethylsulfamoyl chloride, N,N-dimethylformamide, or $CO_2$). The new $R^2$ group so generated can be further modified if necessary.

Scheme 11

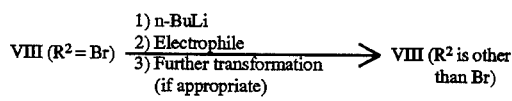

Scheme 12 illustrates the preparation of bicyclic thiophenes of Formula VIIIa (p1=0, 1, 2, 3 or 4) whereby a thiophenethioalkylcarboxylic acid of Formula IX (p1=0, 1, 2, 3 or 4) is treated with a dehydrating reagent such as sulfuric acid, polyphosphoric acid (PPA) or trifluoroacetic anhydride (TFAA). For details of the reaction conditions, please see W. Flemming, et al., *Chem. Ber.* (1925), 58, 1612; I. W. J. Still, et al., *Can. J. Chem.* (1976), 54, 453–470; V. J. Traynelis, et al., *J. Org. Chem.* (1961), 26, 2728; T. K. Jones, et al., *J. Org. Chem.* (1991), 56, 763–769.

Scheme 12

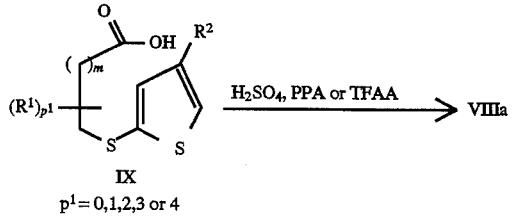

$p^1 = 0,1,2,3$ or 4

Alternatively, the bicyclic thiophenes of Formula VIIIa ($p^1$=0, 1, 2, 3 or 4) can be prepared (Scheme 13) by cyclizing (in the presence of a Lewis acid such as $SnCl_4$) the thiophenethioalkylcarbonyl chlorides of Formula X which are prepared/n situ from the thiophenethioalkylcarboxylic acids of Formula IX ($p^1$=0, 1, 2, 3 or 4) by treatment with a chlorinating reagent such as oxalyl chloride (in the presence of a catalytic amount of N,N-dimethylformamide). This conversion is carried out by methods known in the art (or by obvious modifications of these methods): for example, see E. Dalgliesh, et al., *J. Chem. Soc.* (1945), 893; G. S. Ponticello, et al., *J. Org. Chem.* (1988), 53, 9–13.

Scheme 13

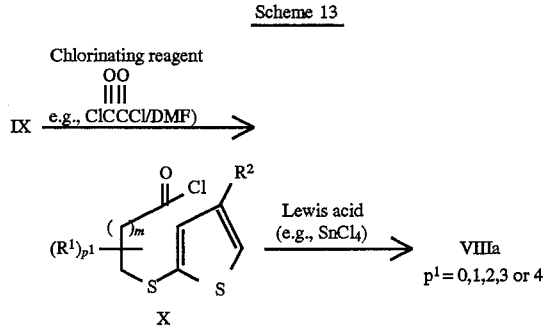

Scheme 14 illustrates the preparation of bicyclic thiophenes of Formula VIIIb (t=1 or 2) whereby an alkenylthiothiophene of Formula XI is treated with a large excess of a strong acid such as trifluoroacetic acid or trifluoromethanesulfonic acid in an inert organic solvent such as methylene chloride or 1,2-dichloroethane at temperatures between 0° C. and 100° C. for a period of time between 1 hour and 5 days. The reaction mixture is then concentrated under reduced pressure. The residue is dissolved in an organic solvent such as methylene chloride or 1,2-dichloroethane and the organic solution is washed with an alkaline aqueous solution such as a 5% sodium bicarbonate aqueous solution. The organic layer is separated, dried over a drying agent such as $MgSO_4$ and concentrated to give the crude product. The crude product can be further purified by chromatography (e.g., silica gel/hexanes).

Scheme 14

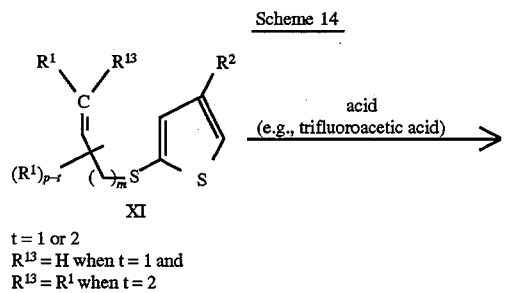

Thiophenethioalkylcarboxylic acids of Formula IX ($p^1$=0, 1, 2, 3 or 4) can be prepared by methods known in the art (or by obvious modifications of these methods): for example, see G. S. Ponticello, et al., *J. Org. Chem.* (1988), 53, 9–13; T. K. Jones, et al., *J. Org. Chem.* (1991), 56, 763–769.

Scheme 15 illustrates the preparation of alkenylthiothiophenes of Formula XI (t=1 or 2; m, p, $R^1$, $R^2$ and $R^{13}$ as defined previously) whereby a thiophenethiol salt of Formula XII (M and $R^2$ are as defined previously) is reacted with an alkenyl halide of Formula XIII ($X^2$=Cl or Br; m, p, t, $R^1$ and $R^{13}$ are as defined previously). The displacement is carried out by methods known in the art (or by obvious modifications of these methods): for example, see J. Z. Mortensen, et al., *Tetrahedron* (1971), 27, 3831–3838; and K. I. Sadykhov, et al., *Khim. Geterotsikl. Soedin.* (1975), 344–345.

Scheme 15

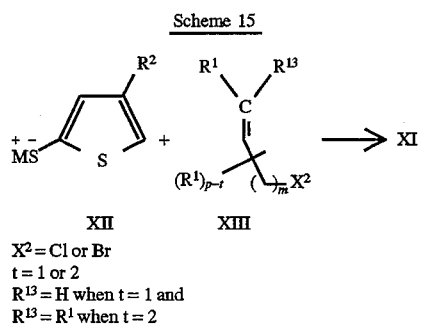

$X^2$ = Cl or Br
t = 1 or 2
$R^{13}$ = H when t = 1 and
$R^{13}$ = $R^1$ when t = 2

Thiophenethiol salts of Formula XII and alkenyl halides of Formula XIII are either commercially available or can be prepared by methods known in the art (or by obvious modifications of these methods).

Scheme 16 illustrates the preparation of compounds of Formula Ie ($R^5$=$R^{5a}$ and $R^{5a}$ is the same as $R^5$ as described in the Summary of the Invention excluding H) whereby a compound of Formula Ie ($R^5$=H) is reacted with a reagent of Formula XIV in the presence of a base wherein $X^4$ is chlorine, bromine, fluorine, OTf, or OAc and $R^{5a}$ is as previously defined. This coupling is carried out by methods known in the art (or by obvious modifications of these methods): for example, see K. Nakamura, et al., WO 95/04054.

Scheme 16

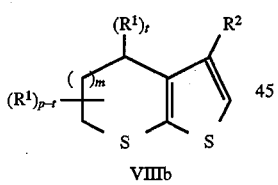

$R^{5a}$ is the same as $R^5$ as described in the Summary of the Invention excluding H Scheme 17 illustrates the preparation of compounds of Formula Ie ($R^5$=H) whereby an ester of Formula XV is reacted with a base such as triethylamine in the presence of a catalytic amount of cyanide source (e.g., acetone cyanohydrin or potassium cyanide). This rearrangement is carried out by methods known in the art (or by obvious modifications of these methods): for example, see W. J. Michaely, EP 369,803.

Scheme 17

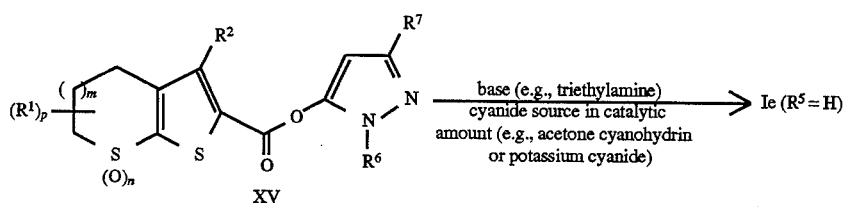

Esters of Formula XV can be prepared by reacting a hydroxypyrazole of Formula XVI with an acid chloride of Formula VI in the presence of a slight mole excess of a base such as triethylamine in an inert organic solvent such as acetonitrile, methylene chloride or toluene at temperatures between 0° C. and 110° C. (Scheme 18). This type of coupling is carried out by methods known in the art (or by obvious modifications of these methods): for example, see W. J. Michaely, EP 369,803.

Scheme 18

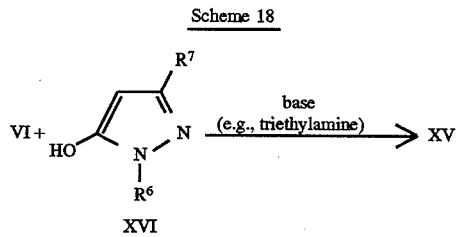

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet.

EXAMPLE 1

Step A: Preparation of 4-methyl-2-[(3-methyl-2-butenyl)thio]thiophene 12.5 mL (0.147 mol) of diisopropylamine was added to 200 mL of tetrahydrofuran and the solution was cooled under nitrogen to about −65° C. 59 mL (0.147 mol) of 2.5M n-butyllithium was added dropwise while keeping the reaction temperature below −55° C. and the mixture was then allowed to stir for 30 min. 13 mL (0.134 mol) of 3-methylthiophene (purchased from Aldrich Chemical Company) was added, the mixture warmed to 0° C. and stirred for 30 min. 5.2 g (0.161 mol) of sulfur was added and, after stirring for 30 min, 20 g (0.134 mol) of 4-bromo-2-methyl-2-butene (purchased from Aldrich Chemical Company) was added dropwise. The mixture was stirred overnight while warming to room temperature and was then evaporated to dryness. The crude product was chromatographed on silica gel eluting with hexane to yield 20.38 g of the title compound of Step A as an oil. $^1$H NMR (CDCl$_3$): δ 1.46 (s,3H), 1.72 (s,3H), 2.2 (s,3H), 3.4 (d,2H), 5.3 (t, 1H), 6.9 (m,2H).

Step B: Preparation of 5,6-dihydro-3,4,4-trimethyl-4H-thieno[2,3-b]thiopyran

A solution of 17.36 g (0.088 mol) of the title compound of Step A in 300 mL of methylene chloride was added dropwise to 300 mL of trifluoroacetic acid under nitrogen. After stirring at room temperature overnight, the mixture was evaporated to dryness. The residue was dissolved in 500 mL of methylene chloride, washed with 5% sodium bicarbonate (2×500 mL), dried (MgSO$_4$), filtered, and evaporated to dryness. The crude product was chromatographed on silica gel eluting with hexane to yield 8.26 g of the title compound of Step B as an oil. $^1$H NMR (CDCl$_3$): δ 1.32 (s,6H), 2.0 (m,2H), 2.3 (s,3H), 3.0 (m,2H), 6.6 (s, 1H).

Step C: Preparation of 5,6-dihydro-3,4,4-trimethyl-4H-thieno[2,3-b]thiopyran-2-carboxylic acid 8.20 g (0.041 mol) of the title compound of Step B was added to 200 mL of tetrahydrofuran under nitrogen. The solution was cooled to about −65° C. and 21 mL (0.053 mol) of 2.5M n-butyllithium was added dropwise while keeping the reaction temperature below −55° C. After stirring for 1 h, an excess of solid CO$_2$ was added in portions and the mixture was allowed to warm to room temperature over 2 hr. The mixture was then diluted with 150 mL of hexane and the precipitate was collected by filtration. The precipitate was added to a mixture of 300 mL of water and 300 mL of methylene chloride, cooled to about 0° C., and then acidified to pH 1 with concentrated hydrochloric acid. The layers were separated and the aqueous layer was extracted with diethyl ether (2×300 mL). The combined organic layers were dried (MgSO$_4$), filtered, and evaporated to dryness to yield 6.36 g of the title compound of Step C as a solid melting at 176°–178° C. $^1$H NMR (DMSO-d$_6$): δ 1.3 (s,6H), 1.95 (m,2H), 2.6 (s,3H), 3.08 (m,2H), 12.7 (br s, 1H).

Step D: Preparation of 5,6-dihydro-3,4,4-trimethyl-4H-thieno[2,3-b]thiopyran-2-carboxylic acid 7,7-dioxide 6.3 g (0.026 mol) of the title compound of Step C was added to 150 mL of methylene chloride. 16.4 mL (0.078 mol) of 32% peracetic acid (purchased from Aldrich Chemical Company) was added to the solution under nitrogen and the mixture stirred overnight at room temperature. 3 mL of dimethylsulfide was added, the reaction mixture was stirred for 15 minutes and then evaporated to dryness. 200 mL of water was added to the residue, triturated, and the product was collected by filtration. The crude product was dissolved in methylene chloride, dried (MgSO$_4$), filtered, and evaporated to dryness to yield 5.50 g of the title compound of Step D as a solid melting at 210°–211° C. $^1$H NMR (DMSO-d$_6$): δ 1.4 (s,6H), 2.3 (m,2H), 2.6 (s,3H), 3.6 (m,2H), 13.7 (br s, 1H).

Step E: Preparation of 3-oxo-1-cyclohexenyl 5,6-dihydro-3,4,4-trimethyl-4H-thieno[2,3-b]thiopyran-2-carboxylate 7,7-dioxide 2.0 g (0.0073 mol) of the title compound of Step D was added to 50 mL of methylene chloride. 1.27 mL (0.0146 mol) of oxalyl chloride (purchased from Janssen) was added followed by 2 drops of N,N-dimethylformamide. The mixture was refluxed under nitrogen for 2 h and then was evaporated to dryness. 50 mL of methylene chloride was added to the residue and then evaporated to dryness. Another 50 mL of methylene chloride was added to the residue and the solution was cooled to about 0° C. 0.90 g (0.0080 mol) of 1,3-cyclohexanedione (purchased from Aldrich Chemical Company) was added followed by 2.8 mL (0.020 mol) of triethylamine, and the mixture was stirred overnight while warming to room temperature. The mixture was evaporated to dryness, the residue was stirred in 100 mL of water and filtered. The crude product was washed with hexane to yield 2.32 g of the title compound of Step E as a solid melting at 133°–134° C. $^1$H NMR (CDCl$_3$): δ 1.48 (s,6H), 2.1 (m,2H), 2.4 (m,4H), 2.6 (m,2H), 2.7 (s,3H), 3.4 (m,2H), 6.06 (s,1H).

Step F: Preparation of 2-[(5,6-dihydro-3,4,4-trimethyl-4H-thieno[2,3-b]thiopyran-2-yl)carbonyl]-1,3-cyclohexanedione S,S-dioxide 2.3 g (0.0065 mol) of the title compound of Step E, 4 drops of acetone cyanohydrin (purchased from Aldrich Chemical Company), and 1.6 mL (0.0113 mol) of triethylamine were added to 50 mL of acetonitrile and allowed to stir at room temperature under nitrogen overnight. The mixture was evaporated to dryness and 25 mL of water was added to the residue. This mixture was acidified to pH 1 with concentrated hydrochloric acid and the product was collected by filtration. The crude product was dissolved in methylene chloride, dried (MgSO$_4$), filtered, and evaporated to dryness to yield 2.07 g of the title compound of Step F, a compound of the invention, as a solid melting at 60° C. (dec.). $^1$H NMR (CDCl$_3$): δ 1.45 (m,6H), 2.1 (m,2H), 2.3 (s,3H), 2.4–2.6 (m,4H), 2.8 (m,2H), 3.4 (m,2H), 16.6 (br s, 1H).

EXAMPLE 2

Step A: Preparation of 1-ethyl-1H-pyrazol-5-yl 5,6-dihydro-3,4,4-trimethyl-4H-thieno[2,3-b]thiopyran-2-carboxylate 7,7-dioxide 2.0 g (0.0073 mol) of the title compound of Step D of Example 1 was added to 50 mL of methylene chloride. 1.27 mL (0.0146 mol) of oxalyl chloride (purchased from Janssen) was added followed by 2 drops of N,N-dimethylformamide. The mixture was refluxed under nitrogen for 2 h and was then evaporated to dryness. 50 mL of methylene chloride was added to the residue and evaporated to dryness. Another 50 mL of methylene chloride was added to the residue and the solution was cooled to about 0° C. 0.90 g (0.0080 mol) of 1-ethyl-1H-pyrazol-5-ol was added to the mixture followed by 2.8 mL (0.0020 mol) of triethylamine and the mixture was stirred overnight while warming to room temperature. The mixture was evaporated to dryness. The residue was stirred in 100 mL of water and the water was decanted. The residue was washed with hexane (2×100 mL) and then chromatographed on silica gel eluting with 4:6 ethyl acetate/hexane to yield 1.57 g of the title compound of Step A as a solid melting at 119°–120° C. $^1$H NMR (CDCl$_3$): δ 1.4 (t, 3H), 1.5 (s, 6H), 2.5 (m, 2H), 2.8 (s, 3H), 3.4 (m, 2H), 4.1 (q, 2H), 6.2 (d, 1H), 7.5 (d, 1H).

Step B: Preparation of (5,6-dihydro-3,4,4-trimethyl-4H-thieno[2,3-b]thiopyran-2-yl)(1-ethyl-5-hydroxy-1H-pyrazol-4-yl)methanone S,S-dioxide 1.5 g (0.0041 mol) of the title compound of Step A, 4 drops of acetone cyanohydrin (purchased from Aldrich Chemical Company), and 1.0 mL (0.0071 mol) of triethylamine were added to 50 mL of acetonitrile and allowed to stir at room temperature under nitrogen overnight. The mixture was evaporated to dryness. 25 mL of water was added to the residue, acidified to pH 1 with concentrated hydrochloric acid, and filtered to yield 1.31 g of the title compound of Step B, a compound of the invention, as a solid melting at 179°–180° C. $^1$H NMR (CDCl$_3$): δ 1.4 (t, 3H), 1.5 (s, 6H), 2.5 (m, 2H), 2.6 (s, 3H), 3.4 (m, 2H), 4.1 (q, 2H), 7.8 (s, 1H).

By the procedures described herein together with methods known in the art, the following compounds of Tables 1 and 2 can be prepared. The following abbreviations are used in the Tables which follow: i-Pr=isopropyl and p-tolyl=4-CH$_3$-phenyl.

TABLE 1 wherein $R^{1a}$, $R^{1c}$ and $R^{1d}$ are H or $R^1$.

| $R^{1a}$ | $R^{1b}$ | $R^{1c}$ | $R^{1d}$ | $R^2$ | $R^3$ | n | m |
|---|---|---|---|---|---|---|---|
| H | H | CH$_3$ | CH$_3$ | CH$_3$ | OH | 2 | 1 |
| H | H | CH$_3$ | CH$_3$ | Cl | OH | 2 | 1 |
| H | H | CH$_3$ | CH$_3$ | Br | OH | 2 | 1 |
| CH$_3$ | CH$_3$ | CH$_3$ | CH$_3$ | CH$_3$ | OH | 2 | 1 |
| CH$_3$ | CH$_3$ | CH$_3$ | CH$_3$ | Cl | OH | 2 | 1 |
| CH$_3$ | CH$_3$ | CH$_3$ | CH$_3$ | Br | OH | 2 | 1 |
| CH$_3$ | H | CH$_3$ | CH$_3$ | CH$_3$ | OH | 2 | 1 |
| CH$_3$ | H | CH$_3$ | CH$_3$ | Cl | OH | 2 | 1 |
| CH$_3$ | H | CH$_3$ | CH$_3$ | Br | OH | 2 | 1 |
| H | H | H$_3$CO | H | CH$_3$ | OH | 2 | 1 |
| H | H | H$_3$CO | H | Cl | OH | 2 | 1 |
| H | H | H$_3$CO | H | Br | OH | 2 | 1 |
| CH$_3$ | CH$_3$ | H$_3$CO | H | CH$_3$ | OH | 2 | 1 |
| CH$_3$ | CH$_3$ | H$_3$CO | H | Cl | OH | 2 | 1 |
| CH$_3$ | CH$_3$ | H$_3$CO | H | Br | OH | 2 | 1 |
| CH$_3$ | H | H$_3$CO | H | CH$_3$ | OH | 2 | 1 |
| CH$_3$ | H | H$_3$CO | H | Cl | OH | 2 | 1 |
| CH$_3$ | H | H$_3$CO | H | Br | OH | 2 | 1 |
| H | H | H$_5$C$_2$O | H | CH$_3$ | OH | 2 | 1 |
| H | H | H$_5$C$_2$O | H | Cl | OH | 2 | 1 |
| H | H | H$_5$C$_2$O | H | Br | OH | 2 | 1 |
| CH$_3$ | CH$_3$ | H$_5$C$_2$O | H | CH$_3$ | OH | 2 | 1 |
| CH$_3$ | CH$_3$ | H$_5$C$_2$O | H | Cl | OH | 2 | 1 |

TABLE 1-continued wherein $R^{1a}$, $R^{1c}$ and $R^{1d}$ are H or $R^1$.

| $R^{1a}$ | $R^{1b}$ | $R^{1c}$ | $R^{1d}$ | $R^2$ | $R^3$ | n | m |
|---|---|---|---|---|---|---|---|
| CH₃ | CH₃ | H₅C₂O | H | Br | OH | 2 | 1 |
| CH₃ | H | H₅C₂O | H | CH₃ | OH | 2 | 1 |
| CH₃ | H | H₅C₂O | H | Cl | OH | 2 | 1 |
| CH₃ | H | H₅C₂O | H | Br | OH | 2 | 1 |
| H | H | i-PrO | H | CH₃ | OH | 2 | 1 |
| H | H | i-PrO | H | Cl | OH | 2 | 1 |
| H | H | i-PrO | H | Br | OH | 2 | 1 |
| CH₃ | CH₃ | i-PrO | H | CH₃ | OH | 2 | 1 |
| CH₃ | CH₃ | i-PrO | H | Cl | OH | 2 | 1 |
| CH₃ | CH₃ | i-PrO | H | Br | OH | 2 | 1 |
| CH₃ | H | i-PrO | H | CH₃ | OH | 2 | 1 |
| CH₃ | H | i-PrO | H | Cl | OH | 2 | 1 |
| CH₃ | H | i-PrO | H | Br | OH | 2 | 1 |
| H | H | H₃CO | CH₃ | CH₃ | OH | 2 | 1 |
| H | H | H₃CO | CH₃ | Cl | OH | 2 | 1 |
| H | H | H₃CO | CH₃ | Br | OH | 2 | 1 |
| CH₃ | CH₃ | H₃CO | CH₃ | CH₃ | OH | 2 | 1 |
| CH₃ | CH₃ | H₃CO | CH₃ | Cl | OH | 2 | 1 |
| CH₃ | CH₃ | H₃CO | CH₃ | Br | OH | 2 | 1 |
| CH₃ | H | H₃CO | CH₃ | CH₃ | OH | 2 | 1 |
| CH₃ | H | H₃CO | CH₃ | Cl | OH | 2 | 1 |
| CH₃ | H | H₃CO | CH₃ | Br | OH | 2 | 1 |
| H | H | O—CH₂CH₂—O | CH₃ | CH₃ | OH | 2 | 1 |
| H | H | O—CH₂CH₂—O | Cl | OH | | 2 | 1 |
| H | H | O—CH₂CH₂—O | Br | OH | | 2 | 1 |
| CH₃ | CH₃ | O—CH₂CH₂—O | CH₃ | OH | | 2 | 1 |
| CH₃ | CH₃ | O—CH₂CH₂—O | Cl | OH | | 2 | 1 |
| CH₃ | CH₃ | O—CH₂CH₂—O | Br | OH | | 2 | 1 |
| CH₃ | H | O—CH₂CH₂—O | CH₃ | OH | | 2 | 1 |
| CH₃ | H | O—CH₂CH₂—O | Cl | OH | | 2 | 1 |
| CH₃ | H | O—CH₂CH₂—O | Br | OH | | 2 | 1 |
| H | H | =N—OCH₃ | CH₃ | OH | | 2 | 1 |
| H | H | =N—OCH₃ | Cl | OH | | 2 | 1 |
| H | H | =N—OCH₃ | Br | OH | | 2 | 1 |
| CH₃ | CH₃ | =N—OCH₃ | CH₃ | OH | | 2 | 1 |
| CH₃ | CH₃ | =N—OCH₃ | Cl | OH | | 2 | 1 |
| CH₃ | CH₃ | =N—OCH₃ | Br | OH | | 2 | 1 |
| CH₃ | H | =N—OCH₃ | CH₃ | OH | | 2 | 1 |
| CH₃ | H | =N—OCH₃ | Cl | OH | | 2 | 1 |
| CH₃ | H | =N—OCH₃ | Br | OH | | 2 | 1 |
| H | H | =N—OC₂H₅ | CH₃ | OH | | 2 | 1 |
| H | H | =N—OC₂H₅ | Cl | OH | | 2 | 1 |
| H | H | =N—OC₂H₅ | Br | OH | | 2 | 1 |
| CH₃ | CH₃ | =N—OC₂H₅ | CH₃ | OH | | 2 | 1 |
| CH₃ | CH₃ | =N—OC₂H₅ | Cl | OH | | 2 | 1 |
| CH₃ | CH₃ | =N—OC₂H₅ | Br | OH | | 2 | 1 |
| CH₃ | H | =N—OC₂H₅ | CH₃ | OH | | 2 | 1 |
| CH₃ | H | =N—OC₂H₅ | Cl | OH | | 2 | 1 |
| CH₃ | H | =N—OC₂H₅ | Br | OH | | 2 | 1 |
| H | H | =N—Oi-Pr | CH₃ | OH | | 2 | 1 |
| H | H | =N—Oi-Pr | Cl | OH | | 2 | 1 |
| H | H | =N—Oi-Pr | Br | OH | | 2 | 1 |
| CH₃ | CH₃ | =N—Oi-Pr | CH₃ | OH | | 2 | 1 |
| CH₃ | CH₃ | =N—Oi-Pr | Cl | OH | | 2 | 1 |
| CH₃ | CH₃ | =N—Oi-Pr | Br | OH | | 2 | 1 |
| CH₃ | H | =N—Oi-Pr | CH₃ | OH | | 2 | 1 |
| CH₃ | H | =N—Oi-Pr | Cl | OH | | 2 | 1 |
| CH₃ | H | =N—Oi-Pr | Br | OH | | 2 | 1 |
| H | H | CH₃ | CH₃ | CH₃ | Cl | 2 | 1 |
| H | H | CH₃ | CH₃ | Cl | Cl | 2 | 1 |
| H | H | CH₃ | CH₃ | Br | Cl | 2 | 1 |
| H | H | CH₃ | CH₃ | CH₃ | OSO₂CH₃ | 2 | 1 |
| H | H | CH₃ | CH₃ | Cl | OSO₂CH₃ | 2 | 1 |
| H | H | CH₃ | CH₃ | Br | OSO₂CH₃ | 2 | 1 |
| H | H | CH₃ | CH₃ | CH₃ | OH | 1 | 1 |
| H | H | CH₃ | CH₃ | Cl | OH | 1 | 1 |
| H | H | CH₃ | CH₃ | Br | OH | 1 | 1 |
| H | H | CH₃ | CH₃ | CH₃ | OH | 0 | 1 |
| H | H | CH₃ | CH₃ | Cl | OH | 0 | 1 |
| H | H | CH₃ | CH₃ | Br | OH | 0 | 1 |
| H | H | CH₃ | CH₃ | CH₃ | OH | 2 | 2 |
| H | H | CH₃ | CH₃ | Cl | OH | 2 | 2 |
| H | H | CH₃ | CH₃ | Br | OH | 2 | 2 |

TABLE 2 wherein $R^{1a}$, $R^{1b}$, $R^{1c}$ and $R^{1d}$ are H or $R^1$

| $R^{1a}$ | $R^{1b}$ | $R^{1c}$ | $R^{1d}$ | $R^2$ | $R^5$ | $R^6$ | $R^7$ | n | m |
|---|---|---|---|---|---|---|---|---|---|
| H | H | CH₃ | CH₃ | CH₃ | H | C₂H₅ | H | 2 | 1 |
| H | H | CH₃ | CH₃ | Cl | H | C₂H₅ | H | 2 | 1 |
| H | H | CH₃ | CH₃ | Br | H | C₂H₅ | H | 2 | 1 |
| CH₃ | CH₃ | CH₃ | CH₃ | CH₃ | H | C₂H₅ | H | 2 | 1 |
| CH₃ | CH₃ | CH₃ | CH₃ | Cl | H | C₂H₅ | H | 2 | 1 |
| CH₃ | CH₃ | CH₃ | CH₃ | Br | H | C₂H₅ | H | 2 | 1 |
| CH₃ | H | CH₃ | CH₃ | CH₃ | H | C₂H₅ | H | 2 | 1 |
| CH₃ | H | CH₃ | CH₃ | Cl | H | C₂H₅ | H | 2 | 1 |
| CH₃ | H | CH₃ | CH₃ | Br | H | C₂H₅ | H | 2 | 1 |
| H | H | H₃CO | H | CH₃ | H | C₂H₅ | H | 2 | 1 |
| H | H | H₃CO | H | Cl | H | C₂H₅ | H | 2 | 1 |

TABLE 2-continued

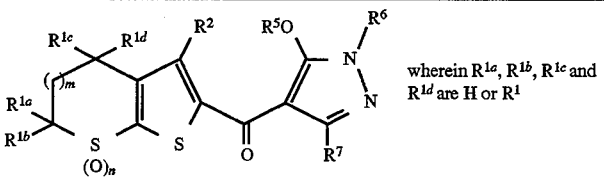

wherein $R^{1a}$, $R^{1b}$, $R^{1c}$ and $R^{1d}$ are H or $R^1$

| $R^{1a}$ | $R^{1b}$ | $R^{1c}$ | $R^{1d}$ | $R^2$ | $R^5$ | $R^6$ | $R^7$ | n | m |
|---|---|---|---|---|---|---|---|---|---|
| H | H | $H_3CO$ | H | Br | H | $C_2H_5$ | H | 2 | 1 |
| $CH_3$ | $CH_3$ | $H_3CO$ | H | $CH_3$ | H | $C_2H_5$ | H | 2 | 1 |
| $CH_3$ | $CH_3$ | $H_3CO$ | H | Cl | H | $C_2H_5$ | H | 2 | 1 |
| $CH_3$ | $CH_3$ | $H_3CO$ | H | Br | H | $C_2H_5$ | H | 2 | 1 |
| $CH_3$ | H | $H_3CO$ | H | $CH_3$ | H | $C_2H_5$ | H | 2 | 1 |
| $CH_3$ | H | $H_3CO$ | H | Cl | H | $C_2H_5$ | H | 2 | 1 |
| $CH_3$ | H | $H_3CO$ | H | Br | H | $C_2H_5$ | H | 2 | 1 |
| H | H | $H_5C_2O$ | H | $CH_3$ | H | $C_2H_5$ | H | 2 | 1 |
| H | H | $H_5C_2O$ | H | Cl | H | $C_2H_5$ | H | 2 | 1 |
| H | H | $H_5C_2O$ | H | Br | H | $C_2H_5$ | H | 2 | 1 |
| $CH_3$ | $CH_3$ | $H_5C_2O$ | H | $CH_3$ | H | $C_2H_5$ | H | 2 | 1 |
| $CH_3$ | $CH_3$ | $H_5C_2O$ | H | Cl | H | $C_2H_5$ | H | 2 | 1 |
| $CH_3$ | $CH_3$ | $H_5C_2O$ | H | Br | H | $C_2H_5$ | H | 2 | 1 |
| $CH_3$ | H | $H_5C_2O$ | H | $CH_3$ | H | $C_2H_5$ | H | 2 | 1 |
| $CH_3$ | H | $H_5C_2O$ | H | Cl | H | $C_2H_5$ | H | 2 | 1 |
| $CH_3$ | H | $H_5C_2O$ | H | Br | H | $C_2H_5$ | H | 2 | 1 |
| H | H | i-PrO | H | $CH_3$ | H | $C_2H_5$ | H | 2 | 1 |
| H | H | i-PrO | H | Cl | H | $C_2H_5$ | H | 2 | 1 |
| H | H | i-PrO | H | Br | H | $C_2H_5$ | H | 2 | 1 |
| $CH_3$ | $CH_3$ | i-PrO | H | $CH_3$ | H | $C_2H_5$ | H | 2 | 1 |
| $CH_3$ | $CH_3$ | i-PrO | H | Cl | H | $C_2H_5$ | H | 2 | 1 |
| $CH_3$ | $CH_3$ | i-PrO | H | Br | H | $C_2H_5$ | H | 2 | 1 |
| $CH_3$ | H | i-PrO | H | $CH_3$ | H | $C_2H_5$ | H | 2 | 1 |
| $CH_3$ | H | i-PrO | H | Cl | H | $C_2H_5$ | H | 2 | 1 |
| $CH_3$ | H | i-PrO | H | Br | H | $C_2H_5$ | H | 2 | 1 |
| H | H | $H_3CO$ | $CH_3$ | $CH_3$ | H | $C_2H_5$ | H | 2 | 1 |
| H | H | $H_3CO$ | $CH_3$ | Cl | H | $C_2H_5$ | H | 2 | 1 |
| H | H | $H_3CO$ | $CH_3$ | Br | H | $C_2H_5$ | H | 2 | 1 |
| $CH_3$ | $CH_3$ | $H_3CO$ | $CH_3$ | $CH_3$ | H | $C_2H_5$ | H | 2 | 1 |
| $CH_3$ | $CH_3$ | $H_3CO$ | $CH_3$ | Cl | H | $C_2H_5$ | H | 2 | 1 |
| $CH_3$ | $CH_3$ | $H_3CO$ | $CH_3$ | Br | H | $C_2H_5$ | H | 2 | 1 |
| $CH_3$ | H | $H_3CO$ | $CH_3$ | $CH_3$ | H | $C_2H_5$ | H | 2 | 1 |
| $CH_3$ | H | $H_3CO$ | $CH_3$ | Cl | H | $C_2H_5$ | H | 2 | 1 |
| $CH_3$ | H | $H_3CO$ | $CH_3$ | Br | H | $C_2H_5$ | H | 2 | 1 |
| H | H | $O-CH_2CH_2-O$ | $CH_3$ | H | $C_2H_5$ | H | 2 | 1 |
| H | H | $O-CH_2CH_2-O$ | Cl | H | $C_2H_5$ | H | 2 | 1 |
| H | H | $O-CH_2CH_2-O$ | Br | H | $C_2H_5$ | H | 2 | 1 |
| $CH_3$ | $CH_3$ | $O-CH_2CH_2-O$ | $CH_3$ | H | $C_2H_5$ | H | 2 | 1 |
| $CH_3$ | $CH_3$ | $O-CH_2CH_2-O$ | Cl | H | $C_2H_5$ | H | 2 | 1 |
| $CH_3$ | $CH_3$ | $O-CH_2CH_2-O$ | Br | H | $C_2H_5$ | H | 2 | 1 |
| $CH_3$ | H | $O-CH_2CH_2-O$ | $CH_3$ | H | $C_2H_5$ | H | 2 | 1 |
| $CH_3$ | H | $O-CH_2CH_2-O$ | Cl | H | $C_2H_5$ | H | 2 | 1 |
| $CH_3$ | H | $O-CH_2CH_2-O$ | Br | H | $C_2H_5$ | H | 2 | 1 |
| H | H | $=N-OCH_3$ | $CH_3$ | H | $C_2H_5$ | H | 2 | 1 |
| H | H | $=N-OCH_3$ | Cl | H | $C_2H_5$ | H | 2 | 1 |
| H | H | $=N-OCH_3$ | Br | H | $C_2H_5$ | H | 2 | 1 |
| $CH_3$ | $CH_3$ | $=N-OCH_3$ | $CH_3$ | H | $C_2H_5$ | H | 2 | 1 |
| $CH_3$ | $CH_3$ | $=N-OCH_3$ | Cl | H | $C_2H_5$ | H | 2 | 1 |
| $CH_3$ | $CH_3$ | $=N-OCH_3$ | Br | H | $C_2H_5$ | H | 2 | 1 |
| $CH_3$ | H | $=N-OCH_3$ | $CH_3$ | H | $C_2H_5$ | H | 2 | 1 |
| $CH_3$ | H | $=N-OCH_3$ | Cl | H | $C_2H_5$ | H | 2 | 1 |
| $CH_3$ | H | $=N-OCH_3$ | Br | H | $C_2H_5$ | H | 2 | 1 |
| H | H | $=N-OC_2H_5$ | $CH_3$ | H | $C_2H_5$ | H | 2 | 1 |
| H | H | $=N-OC_2H_5$ | Cl | H | $C_2H_5$ | H | 2 | 1 |
| H | H | $=N-OC_2H_5$ | Br | H | $C_2H_5$ | H | 2 | 1 |
| $CH_3$ | $CH_3$ | $=N-OC_2H_5$ | $CH_3$ | H | $C_2H_5$ | H | 2 | 1 |
| $CH_3$ | $CH_3$ | $=N-OC_2H_5$ | Cl | H | $C_2H_5$ | H | 2 | 1 |
| $CH_3$ | $CH_3$ | $=N-OC_2H_5$ | Br | H | $C_2H_5$ | H | 2 | 1 |
| $CH_3$ | H | $=N-OC_2H_5$ | $CH_3$ | H | $C_2H_5$ | H | 2 | 1 |
| $CH_3$ | H | $=N-OC_2H_5$ | Cl | H | $C_2H_5$ | H | 2 | 1 |
| $CH_3$ | H | $=N-OC_2H_5$ | Br | H | $C_2H_5$ | H | 2 | 1 |
| H | H | $=N-O-i-Pr$ | $CH_3$ | H | $C_2H_5$ | H | 2 | 1 |
| H | H | $=N-O-i-Pr$ | Cl | H | $C_2H_5$ | H | 2 | 1 |
| H | H | $=N-O-i-Pr$ | Br | H | $C_2H_5$ | H | 2 | 1 |
| $CH_3$ | $CH_3$ | $=N-O-i-Pr$ | $CH_3$ | H | $C_2H_5$ | H | 2 | 1 |
| $CH_3$ | $CH_3$ | $=N-O-i-Pr$ | Cl | H | $C_2H_5$ | H | 2 | 1 |
| $CH_3$ | $CH_3$ | $=N-O-i-Pr$ | Br | H | $C_2H_5$ | H | 2 | 1 |
| $CH_3$ | H | $=N-O-i-Pr$ | $CH_3$ | H | $C_2H_5$ | H | 2 | 1 |

TABLE 2-continued wherein $R^{1a}$, $R^{1b}$, $R^{1c}$ and $R^{1d}$ are H or $R^1$

| $R^{1a}$ | $R^{1b}$ | $R^{1c}$ | $R^{1d}$ | $R^2$ | $R^5$ | $R^6$ | $R^7$ | n | m |
|---|---|---|---|---|---|---|---|---|---|
| $CH_3$ | H | =N—O-i-Pr | | Cl | H | $C_2H_5$ | H | 2 | 1 |
| $CH_3$ | H | =N—O-i-Pr | | Br | H | $C_2H_5$ | H | 2 | 1 |
| H | H | $CH_3$ | $CH_3$ | $CH_3$ | H | $C_2H_5$ | H | 1 | 1 |
| H | H | $CH_3$ | $CH_3$ | Cl | H | $C_2H_5$ | H | 1 | 1 |
| H | H | $CH_3$ | $CH_3$ | Br | H | $C_2H_5$ | H | 1 | 1 |
| H | H | $CH_3$ | $CH_3$ | $CH_3$ | H | $C_2H_5$ | H | 0 | 1 |
| H | H | $CH_3$ | $CH_3$ | Cl | H | $C_2H_5$ | H | 0 | 1 |
| H | H | $CH_3$ | $CH_3$ | Br | H | $C_2H_5$ | H | 0 | 1 |
| H | H | $CH_3$ | $CH_3$ | $CH_3$ | H | $C_2H_5$ | H | 2 | 2 |
| H | H | $CH_3$ | $CH_3$ | Cl | H | $C_2H_5$ | H | 2 | 2 |
| H | H | $CH_3$ | $CH_3$ | Br | H | $C_2H_5$ | H | 2 | 2 |
| H | H | $CH_3$ | $CH_3$ | $CH_3$ | $SO_2CH_3$ | $C_2H_5$ | H | 2 | 1 |
| H | H | $CH_3$ | $CH_3$ | Cl | $SO_2CH_3$ | $C_2H_5$ | H | 2 | 1 |
| H | H | $CH_3$ | $CH_3$ | Br | $SO_2CH_3$ | $C_2H_5$ | H | 2 | 1 |
| H | H | $CH_3$ | $CH_3$ | $CH_3$ | $SO_2C_2H_5$ | $C_2H_5$ | H | 2 | 1 |
| H | H | $CH_3$ | $CH_3$ | Cl | $SO_2C_2H_5$ | $C_2H_5$ | H | 2 | 1 |
| H | H | $CH_3$ | $CH_3$ | Br | $SO_2C_2H_5$ | $C_2H_5$ | H | 2 | 1 |
| H | H | $CH_3$ | $CH_3$ | $CH_3$ | $SO_2$-n-$C_3H_7$ | $C_2H_5$ | H | 2 | 1 |
| H | H | $CH_3$ | $CH_3$ | Cl | $SO_2$-n-$C_3H_7$ | $C_2H_5$ | H | 2 | 1 |
| H | H | $CH_3$ | $CH_3$ | Br | $SO_2$-n-$C_3H_7$ | $C_2H_5$ | H | 2 | 1 |
| H | H | $CH_3$ | $CH_3$ | $CH_3$ | $SO_2$-n-$C_4H_9$ | $C_2H_5$ | H | 2 | 1 |
| H | H | $CH_3$ | $CH_3$ | Cl | $SO_2$-n-$C_4H_9$ | $C_2H_5$ | H | 2 | 1 |
| H | H | $CH_3$ | $CH_3$ | Br | $SO_2$-n-$C_4H_9$ | $C_2H_5$ | H | 2 | 1 |
| H | H | $CH_3$ | $CH_3$ | $CH_3$ | $SO_2$-p-tolyl | $C_2H_5$ | H | 2 | 1 |
| H | H | $CH_3$ | $CH_3$ | Cl | $SO_2$-p-tolyl | $C_2H_5$ | H | 2 | 1 |
| H | H | $CH_3$ | $CH_3$ | Br | $SO_2$-p-tolyl | $C_2H_5$ | H | 2 | 1 |
| H | H | $CH_3$ | $CH_3$ | $CH_3$ | $SO_2$-p-$NO_2C_6H_5$ | $C_2H_5$ | H | 2 | 1 |
| H | H | $CH_3$ | $CH_3$ | Cl | $SO_2$-p-$NO_2C_6H_5$ | $C_2H_5$ | H | 2 | 1 |
| H | H | $CH_3$ | $CH_3$ | Br | $SO_2$-p-$NO_2C_6H_5$ | $C_2H_5$ | H | 2 | 1 |
| H | H | $CH_3$ | $CH_3$ | $CH_3$ | $SO_2$-p-$ClC_6H_5$ | $C_2H_5$ | H | 2 | 1 |
| H | H | $CH_3$ | $CH_3$ | Cl | $SO_2$-p-$ClC_6H_5$ | $C_2H_5$ | H | 2 | 1 |
| H | H | $CH_3$ | $CH_3$ | Br | $SO_2$-p-$ClC_6H_5$ | $C_2H_5$ | H | 2 | 1 |
| H | H | $CH_3$ | $CH_3$ | $CH_3$ | C(=O)$CH_3$ | $C_2H_5$ | H | 2 | 1 |
| H | H | $CH_3$ | $CH_3$ | Cl | C(=O)$CH_3$ | $C_2H_5$ | H | 2 | 1 |
| H | H | $CH_3$ | $CH_3$ | Br | C(=O)$CH_3$ | $C_2H_5$ | H | 2 | 1 |
| H | H | $CH_3$ | $CH_3$ | $CH_3$ | C(=O)$C_2H_5$ | $C_2H_5$ | H | 2 | 1 |
| H | H | $CH_3$ | $CH_3$ | Cl | C(=O)$C_2H_5$ | $C_2H_5$ | H | 2 | 1 |
| H | H | $CH_3$ | $CH_3$ | Br | C(=O)$C_2H_5$ | $C_2H_5$ | H | 2 | 1 |
| H | H | $CH_3$ | $CH_3$ | $CH_3$ | H | $CH_3$ | H | 2 | 1 |
| H | H | $CH_3$ | $CH_3$ | Cl | H | $CH_3$ | H | 2 | 1 |
| H | H | $CH_3$ | $CH_3$ | Br | H | $CH_3$ | H | 2 | 1 |
| H | H | $CH_3$ | $CH_3$ | $CH_3$ | $SO_2$-n-$C_3H_7$ | $CH_3$ | H | 2 | 1 |
| H | H | $CH_3$ | $CH_3$ | Cl | $SO_2$-n-$C_3H_7$ | $CH_3$ | H | 2 | 1 |
| H | H | $CH_3$ | $CH_3$ | Br | $SO_2$-n-$C_3H_7$ | $CH_3$ | H | 2 | 1 |
| H | H | $CH_3$ | $CH_3$ | $CH_3$ | $SO_2$-p-tolyl | $CH_3$ | H | 2 | 1 |
| H | H | $CH_3$ | $CH_3$ | Cl | $SO_2$-p-tolyl | $CH_3$ | H | 2 | 1 |
| H | H | $CH_3$ | $CH_3$ | Br | $SO_2$-p-tolyl | $CH_3$ | H | 2 | 1 |
| H | H | $H_3CO$ | H | $CH_3$ | $SO_2CH_3$ | $C_2H_5$ | H | 2 | 1 |
| H | H | $H_3CO$ | H | Cl | $SO_2CH_3$ | $C_2H_5$ | H | 2 | 1 |
| H | H | $H_3CO$ | H | Br | $SO_2CH_3$ | $C_2H_5$ | H | 2 | 1 |
| H | H | $H_3CO$ | H | $CH_3$ | $SO_2C_2H_5$ | $C_2H_5$ | H | 2 | 1 |
| H | H | $H_3CO$ | H | Cl | $SO_2C_2H_5$ | $C_2H_5$ | H | 2 | 1 |
| H | H | $H_3CO$ | H | Br | $SO_2C_2H_5$ | $C_2H_5$ | H | 2 | 1 |
| H | H | $H_3CO$ | H | $CH_3$ | $SO_2$-n-$C_3H_7$ | $C_2H_5$ | H | 2 | 1 |
| H | H | $H_3CO$ | H | Cl | $SO_2$-n-$C_3H_7$ | $C_2H_5$ | H | 2 | 1 |
| H | H | $H_3CO$ | H | Br | $SO_2$-n-$C_3H_7$ | $C_2H_5$ | H | 2 | 1 |
| H | H | $H_3CO$ | H | $CH_3$ | $SO_2$-n-$C_4H_9$ | $C_2H_5$ | H | 2 | 1 |
| H | H | $H_3CO$ | H | Cl | $SO_2$-n-$C_4H_9$ | $C_2H_5$ | H | 2 | 1 |
| H | H | $H_3CO$ | H | Br | $SO_2$-n-$C_4H_9$ | $C_2H_5$ | H | 2 | 1 |
| H | H | $H_3CO$ | H | $CH_3$ | $SO_2$-p-tolyl | $C_2H_5$ | H | 2 | 1 |
| H | H | $H_3CO$ | H | Cl | $SO_2$-p-tolyl | $C_2H_5$ | H | 2 | 1 |
| H | H | $H_3CO$ | H | Br | $SO_2$-p-tolyl | $C_2H_5$ | H | 2 | 1 |
| H | H | $H_3CO$ | H | $CH_3$ | $SO_2$-p-$NO_2C_6H_5$ | $C_2H_5$ | H | 2 | 1 |
| H | H | $H_3CO$ | H | Cl | $SO_2$-p-$NO_2C_6H_5$ | $C_2H_5$ | H | 2 | 1 |
| H | H | $H_3CO$ | H | Br | $SO_2$-p-$NO_2C_6H_5$ | $C_2H_5$ | H | 2 | 1 |
| H | H | $H_3CO$ | H | $CH_3$ | $SO_2$-p-$ClC_6H_5$ | $C_2H_5$ | H | 2 | 1 |
| H | H | $H_3CO$ | H | Cl | $SO_2$-p-$ClC_6H_5$ | $C_2H_5$ | H | 2 | 1 |
| H | H | $H_3CO$ | H | Br | $SO_2$-p-$ClC_6H_5$ | $C_2H_5$ | H | 2 | 1 |

TABLE 2-continued

| R¹ᵃ | R¹ᵇ | R¹ᶜ | R¹ᵈ | R² | R⁵ | R⁶ | R⁷ | n | m |
|---|---|---|---|---|---|---|---|---|---|
| H | H | H₃CO | H | CH₃ | C(=O)CH₃ | C₂H₅ | H | 2 | 1 |
| H | H | H₃CO | H | Cl | C(=O)CH₃ | C₂H₅ | H | 2 | 1 |
| H | H | H₃CO | H | Br | C(=O)CH₃ | C₂H₅ | H | 2 | 1 |
| H | H | H₃CO | H | CH₃ | C(=O)C₂H₅ | C₂H₅ | H | 2 | 1 |
| H | H | H₃CO | H | Cl | C(=O)C₂H₅ | C₂H₅ | H | 2 | 1 |
| H | H | H₃CO | H | Br | C(=O)C₂H₅ | C₂H₅ | H | 2 | 1 |
| H | H | H₃CO | H | CH₃ | H | CH₃ | H | 2 | 1 |
| H | H | H₃CO | H | Cl | H | CH₃ | H | 2 | 1 |
| H | H | H₃CO | H | Br | H | CH₃ | H | 2 | 1 |
| H | H | H₃CO | H | CH₃ | SO₂-n-C₃H₇ | CH₃ | H | 2 | 1 |
| H | H | H₃CO | H | Cl | SO₂-n-C₃H₇ | CH₃ | H | 2 | 1 |
| H | H | H₃CO | H | Br | SO₂-n-C₃H₇ | CH₃ | H | 2 | 1 |
| H | H | H₃CO | H | CH₃ | SO₂-p-tolyl | CH₃ | H | 2 | 1 |
| H | H | H₃CO | H | Cl | SO₂-p-tolyl | CH₃ | H | 2 | 1 |
| H | H | H₃CO | H | Br | SO₂-p-tolyl | CH₃ | H | 2 | 1 |
| H | H | O—CH₂CH₂—O | | CH₃ | SO₂CH₃ | C₂H₅ | H | 2 | 1 |
| H | H | O—CH₂CH₂—O | | Cl | SO₂CH₃ | C₂H₅ | H | 2 | 1 |
| H | H | O—CH₂CH₂—O | | Br | SO₂CH₃ | C₂H₅ | H | 2 | 1 |
| H | H | O—CH₂CH₂—O | | CH₃ | SO₂C₂H₅ | C₂H₅ | H | 2 | 1 |
| H | H | O—CH₂CH₂—O | | Cl | SO₂C₂H₅ | C₂H₅ | H | 2 | 1 |
| H | H | O—CH₂CH₂—O | | Br | SO₂C₂H₅ | C₂H₅ | H | 2 | 1 |
| H | H | O—CH₂CH₂—O | | CH₃ | SO₂-n-C₃H₇ | C₂H₅ | H | 2 | 1 |
| H | H | O—CH₂CH₂—O | | Cl | SO₂-n-C₃H₇ | C₂H₅ | H | 2 | 1 |
| H | H | O—CH₂CH₂—O | | Br | SO₂-n-C₃H₇ | C₂H₅ | H | 2 | 1 |
| H | H | O—CH₂CH₂—O | | CH₃ | SO₂-n-C₄H₉ | C₂H₅ | H | 2 | 1 |
| H | H | O—CH₂CH₂—O | | Cl | SO₂-n-C₄H₉ | C₂H₅ | H | 2 | 1 |
| H | H | O—CH₂CH₂—O | | Br | SO₂-n-C₄H₉ | C₂H₅ | H | 2 | 1 |
| H | H | O—CH₂CH₂—O | | CH₃ | SO₂-p-tolyl | C₂H₅ | H | 2 | 1 |
| H | H | O—CH₂CH₂—O | | Cl | SO₂-p-tolyl | C₂H₅ | H | 2 | 1 |
| H | H | O—CH₂CH₂—O | | Br | SO₂-p-tolyl | C₂H₅ | H | 2 | 1 |
| H | H | O—CH₂CH₂—O | | CH₃ | SO₂-p-NO₂C₆H₅ | C₂H₅ | H | 2 | 1 |
| H | H | O—CH₂CH₂—O | | Cl | SO₂-p-NO₂C₆H₅ | C₂H₅ | H | 2 | 1 |
| H | H | O—CH₂CH₂—O | | Br | SO₂-p-NO₂C₆H₅ | C₂H₅ | H | 2 | 1 |
| H | H | O—CH₂CH₂—O | | CH₃ | SO₂-p-ClC₆H₅ | C₂H₅ | H | 2 | 1 |
| H | H | O—CH₂CH₂—O | | Cl | SO₂-p-ClC₆H₅ | C₂H₅ | H | 2 | 1 |
| H | H | O—CH₂CH₂—O | | Br | SO₂-p-ClC₆H₅ | C₂H₅ | H | 2 | 1 |
| H | H | O—CH₂CH₂—O | | CH₃ | C(=O)CH₃ | C₂H₅ | H | 2 | 1 |
| H | H | O—CH₂CH₂—O | | Cl | C(=O)CH₃ | C₂H₅ | H | 2 | 1 |
| H | H | O—CH₂CH₂—O | | Br | C(=O)CH₃ | C₂H₅ | H | 2 | 1 |
| H | H | O—CH₂CH₂—O | | CH₃ | C(=O)C₂H₅ | C₂H₅ | H | 2 | 1 |
| H | H | O—CH₂CH₂—O | | Cl | C(=O)C₂H₅ | C₂H₅ | H | 2 | 1 |
| H | H | O—CH₂CH₂—O | | Br | C(=O)C₂H₅ | C₂H₅ | H | 2 | 1 |
| H | H | O—CH₂CH₂—O | | CH₃ | H | CH₃ | H | 2 | 1 |
| H | H | O—CH₂CH₂—O | | Cl | H | CH₃ | H | 2 | 1 |
| H | H | O—CH₂CH₂—O | | Br | H | CH₃ | H | 2 | 1 |
| H | H | O—CH₂CH₂—O | | CH₃ | SO₂-n-C₃H₇ | CH₃ | H | 2 | 1 |
| H | H | O—CH₂CH₂—O | | Cl | SO₂-n-C₃H₇ | CH₃ | H | 2 | 1 |
| H | H | O—CH₂CH₂—O | | Br | SO₂-n-C₃H₇ | CH₃ | H | 2 | 1 |
| H | H | O—CH₂CH₂—O | | CH₃ | SO₂-p-tolyl | CH₃ | H | 2 | 1 |
| H | H | O—CH₂CH₂—O | | Cl | SO₂-p-tolyl | CH₃ | H | 2 | 1 |
| H | H | O—CH₂CH₂—O | | Br | SO₂-p-tolyl | CH₃ | H | 2 | 1 |
| H | H | =N—OCH₃ | | CH₃ | SO₂CH₃ | C₂H₅ | H | 2 | 1 |
| H | H | =N—OCH₃ | | Cl | SO₂CH₃ | C₂H₅ | H | 2 | 1 |
| H | H | =N—OCH₃ | | Br | SO₂CH₃ | C₂H₅ | H | 2 | 1 |
| H | H | =N—OCH₃ | | CH₃ | SO₂C₂H₅ | C₂H₅ | H | 2 | 1 |
| H | H | =N—OCH₃ | | Cl | SO₂C₂H₅ | C₂H₅ | H | 2 | 1 |
| H | H | =N—OCH₃ | | Br | SO₂C₂H₅ | C₂H₅ | H | 2 | 1 |
| H | H | =N—OCH₃ | | CH₃ | SO₂-n-C₃H₇ | C₂H₅ | H | 2 | 1 |
| H | H | =N—OCH₃ | | Cl | SO₂-n-C₃H₇ | C₂H₅ | H | 2 | 1 |
| H | H | =N—OCH₃ | | Br | SO₂-n-C₃H₇ | C₂H₅ | H | 2 | 1 |
| H | H | =N—OCH₃ | | CH₃ | SO₂-n-C₄H₉ | C₂H₅ | H | 2 | 1 |
| H | H | =N—OCH₃ | | Cl | SO₂-n-C₄H₉ | C₂H₅ | H | 2 | 1 |
| H | H | =N—OCH₃ | | Br | SO₂-n-C₄H₉ | C₂H₅ | H | 2 | 1 |
| H | H | =N—OCH₃ | | CH₃ | SO₂-p-tolyl | C₂H₅ | H | 2 | 1 |
| H | H | =N—OCH₃ | | Cl | SO₂-p-tolyl | C₂H₅ | H | 2 | 1 |
| H | H | =N—OCH₃ | | Br | SO₂-p-tolyl | C₂H₅ | H | 2 | 1 |
| H | H | =N—OCH₃ | | CH₃ | SO₂-p-NO₂C₆H₅ | C₂H₅ | H | 2 | 1 |
| H | H | =N—OCH₃ | | Cl | SO₂-p-NO₂C₆H₅ | C₂H₅ | H | 2 | 1 |

TABLE 2-continued

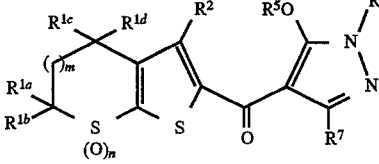

wherein $R^{1a}$, $R^{1b}$, $R^{1c}$ and $R^{1d}$ are H or $R^1$

| $R^{1a}$ | $R^{1b}$ | $R^{1c}$ | $R^{1d}$ | $R^2$ | $R^5$ | $R^6$ | $R^7$ | n | m |
|---|---|---|---|---|---|---|---|---|---|
| H | H | =N—OCH$_3$ | Br | SO$_2$-p-NO$_2$C$_6$H$_5$ | C$_2$H$_5$ | H | 2 | 1 |
| H | H | =N—OCH$_3$ | CH$_3$ | SO$_2$-p-ClC$_6$H$_5$ | C$_2$H$_5$ | H | 2 | 1 |
| H | H | =N—OCH$_3$ | Cl | SO$_2$-p-ClC$_6$H$_5$ | C$_2$H$_5$ | H | 2 | 1 |
| H | H | =N—OCH$_3$ | Br | SO$_2$-p-ClC$_6$H$_5$ | C$_2$H$_5$ | H | 2 | 1 |
| H | H | =N—OCH$_3$ | CH$_3$ | C(=O)CH$_3$ | C$_2$H$_5$ | H | 2 | 1 |
| H | H | =N—OCH$_3$ | Cl | C(=O)CH$_3$ | C$_2$H$_5$ | H | 2 | 1 |
| H | H | =N—OCH$_3$ | Br | C(=O)CH$_3$ | C$_2$H$_5$ | H | 2 | 1 |
| H | H | =N—OCH$_3$ | CH$_3$ | C(=O)C$_2$H$_5$ | C$_2$H$_5$ | H | 2 | 1 |
| H | H | =N—OCH$_3$ | Cl | C(=O)C$_2$H$_5$ | C$_2$H$_5$ | H | 2 | 1 |
| H | H | =N—OCH$_3$ | Br | C(=O)C$_2$H$_5$ | C$_2$H$_5$ | H | 2 | 1 |
| H | H | =N—OCH$_3$ | CH$_3$ | H | CH$_3$ | H | 2 | 1 |
| H | H | =N—OCH$_3$ | Cl | H | CH$_3$ | H | 2 | 1 |
| H | H | =N—OCH$_3$ | Br | H | CH$_3$ | H | 2 | 1 |
| H | H | =N—OCH$_3$ | CH$_3$ | SO$_2$-n-C$_3$H$_7$ | CH$_3$ | H | 2 | 1 |
| H | H | =N—OCH$_3$ | Cl | SO$_2$-n-C$_3$H$_7$ | CH$_3$ | H | 2 | 1 |
| H | H | =N—OCH$_3$ | Br | SO$_2$-n-C$_3$H$_7$ | CH$_3$ | H | 2 | 1 |
| H | H | =N—OCH$_3$ | CH$_3$ | SO$_2$-p-tolyl | CH$_3$ | H | 2 | 1 |
| H | H | =N—OCH$_3$ | Cl | SO$_2$-p-tolyl | CH$_3$ | H | 2 | 1 |
| H | H | =N—OCH$_3$ | Br | SO$_2$-p-tolyl | CH$_3$ | H | 2 | 1 |
| H | H | =N—OC$_2$H$_5$ | CH$_3$ | SO$_2$CH$_3$ | C$_2$H$_5$ | H | 2 | 1 |
| H | H | =N—OC$_2$H$_5$ | Cl | SO$_2$CH$_3$ | C$_2$H$_5$ | H | 2 | 1 |
| H | H | =N—OC$_2$H$_5$ | Br | SO$_2$CH$_3$ | C$_2$H$_5$ | H | 2 | 1 |
| H | H | =N—OC$_2$H$_5$ | CH$_3$ | SO$_2$C$_2$H$_5$ | C$_2$H$_5$ | H | 2 | 1 |
| H | H | =N—OC$_2$H$_5$ | Cl | SO$_2$C$_2$H$_5$ | C$_2$H$_5$ | H | 2 | 1 |
| H | H | =N—OC$_2$H$_5$ | Br | SO$_2$C$_2$H$_5$ | C$_2$H$_5$ | H | 2 | 1 |
| H | H | =N—OC$_2$H$_5$ | CH$_3$ | SO$_2$-n-C$_3$H$_7$ | C$_2$H$_5$ | H | 2 | 1 |
| H | H | =N—OC$_2$H$_5$ | Cl | SO$_2$-n-C$_3$H$_7$ | C$_2$H$_5$ | H | 2 | 1 |
| H | H | =N—OC$_2$H$_5$ | Br | SO$_2$-n-C$_3$H$_7$ | C$_2$H$_5$ | H | 2 | 1 |
| H | H | =N—OC$_2$H$_5$ | CH$_3$ | SO$_2$-n-C$_4$H$_9$ | C$_2$H$_5$ | H | 2 | 1 |
| H | H | =N—OC$_2$H$_5$ | Cl | SO$_2$-n-C$_4$H$_9$ | C$_2$H$_5$ | H | 2 | 1 |
| H | H | =N—OC$_2$H$_5$ | Br | SO$_2$-n-C$_4$H$_9$ | C$_2$H$_5$ | H | 2 | 1 |
| H | H | =N—OC$_2$H$_5$ | CH$_3$ | SO$_2$-p-tolyl | C$_2$H$_5$ | H | 2 | 1 |
| H | H | =N—OC$_2$H$_5$ | Cl | SO$_2$-p-tolyl | C$_2$H$_5$ | H | 2 | 1 |
| H | H | =N—OC$_2$H$_5$ | Br | SO$_2$-p-tolyl | C$_2$H$_5$ | H | 2 | 1 |
| H | H | =N—OC$_2$H$_5$ | CH$_3$ | SO$_2$-p-NO$_2$C$_6$H$_5$ | C$_2$H$_5$ | H | 2 | 1 |
| H | H | =N—OC$_2$H$_5$ | Cl | SO$_2$-p-NO$_2$C$_6$H$_5$ | C$_2$H$_5$ | H | 2 | 1 |
| H | H | =N—OC$_2$H$_5$ | Br | SO$_2$-p-NO$_2$C$_6$H$_5$ | C$_2$H$_5$ | H | 2 | 1 |
| H | H | =N—OC$_2$H$_5$ | CH$_3$ | SO$_2$-p-ClC$_6$H$_5$ | C$_2$H$_5$ | H | 2 | 1 |
| H | H | =N—OC$_2$H$_5$ | Cl | SO$_2$-p-ClC$_6$H$_5$ | C$_2$H$_5$ | H | 2 | 1 |
| H | H | =N—OC$_2$H$_5$ | Br | SO$_2$-p-ClC$_6$H$_5$ | C$_2$H$_5$ | H | 2 | 1 |
| H | H | =N—OC$_2$H$_5$ | CH$_3$ | C(=O)CH$_3$ | C$_2$H$_5$ | H | 2 | 1 |
| H | H | =N—OC$_2$H$_5$ | Cl | C(=O)CH$_3$ | C$_2$H$_5$ | H | 2 | 1 |
| H | H | =N—OC$_2$H$_5$ | Br | C(=O)CH$_3$ | C$_2$H$_5$ | H | 2 | 1 |
| H | H | =N—OC$_2$H$_5$ | CH$_3$ | C(=O)C$_2$H$_5$ | C$_2$H$_5$ | H | 2 | 1 |
| H | H | =N—OC$_2$H$_5$ | Cl | C(=O)C$_2$H$_5$ | C$_2$H$_5$ | H | 2 | 1 |
| H | H | =N—OC$_2$H$_5$ | Br | C(=O)C$_2$H$_5$ | C$_2$H$_5$ | H | 2 | 1 |
| H | H | =N—OC$_2$H$_5$ | CH$_3$ | H | CH$_3$ | H | 2 | 1 |
| H | H | =N—OC$_2$H$_5$ | Cl | H | CH$_3$ | H | 2 | 1 |
| H | H | =N—OC$_2$H$_5$ | Br | H | CH$_3$ | H | 2 | 1 |
| H | H | =N—OC$_2$H$_5$ | CH$_3$ | SO$_2$-n-C$_3$H$_7$ | CH$_3$ | H | 2 | 1 |
| H | H | =N—OC$_2$H$_5$ | Cl | SO$_2$-n-C$_3$H$_7$ | CH$_3$ | H | 2 | 1 |
| H | H | =N—OC$_2$H$_5$ | Br | SO$_2$-n-C$_3$H$_7$ | CH$_3$ | H | 2 | 1 |
| H | H | =N—OC$_2$H$_5$ | CH$_3$ | SO$_2$-p-tolyl | CH$_3$ | H | 2 | 1 |
| H | H | =N—OC$_2$H$_5$ | Cl | SO$_2$-p-tolyl | CH$_3$ | H | 2 | 1 |
| H | H | =N—OC$_2$H$_5$ | Br | SO$_2$-p-tolyl | CH$_3$ | H | 2 | 1 |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, N.Y., 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299, 566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A and B.

| Example A | |
| --- | --- |
| High Strength Concentrate | |
| Compound 2 | 98.5% |
| silica aerogel | 0.5% |
| synthetic amorphous fine silica | 1.0%. |

| Example B | |
| --- | --- |
| Wettable Powder | |
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

| Example C | |
| --- | --- |
| Granule | |
| Compound 2 | 10.0% |
| attapulgite granules (low volatile matter, 0.71/0.30 mm; U.S.S. No. 25–50 sieves) | 90.0%. |

| Example D | |
| --- | --- |
| Extruded Pellet | |
| Compound 2 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4-(1-methylethyl)-5-oxo-1H-imidazol-2-yl]-5-methyl-3-pyridinecarboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α,2-dichloro-5-[4-(difluoromethyl)-4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, fluridone, flurochloridone, fluroxypyr, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox (AC 299 263), imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole (RPA 201772), lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2-chloro-4-fluoro-5-[(tetrahydro-3-oxo-1H, 3H-[1,3,4]thiadiazolo[3,4-a]pyridazin-1-ylidene)amino]phenyl]thioacetate (KIH 9201), methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl)amino]carbonyl]amino]sulfonyl]-1-(2-pyridinyl)-1H-pyrazole-4-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, 3-oxetanyl 2-[[[[(4,6-dimethyl-2-pyrimidinyl)amino]carbonyl]amino]sulfonyl]benzoate (CGA 277476), oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds. Compounds of the sulfonylurea, imidazolinone and triazolopyrimidine classes as well as benzoic acids and phenoxy compounds are contemplated. The preferred mixing partners are selected from the group rimsulfuron, nicosulfuron, chlorimuron ethyl, imazethapyr and dicamba. Most preferred mixing partners are rimsulfuron and imazethapyr.

An herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control.

The following Tests demonstrate the control efficacy of the compounds of this invention against specific weeds. The weed control afforded by the compounds is not limited, however, to these species. See Index Tables A and B for compound descriptions. The abbreviation "dec" indicates that the compound appeared to decompose on melting. The abbreviation "Ex." stands for "Example" and is followed by a number indicating in which example the compound is prepared.

Index TABLE A

[Structure: cyclohexane-1,3-dione linked to a thiophene ring bearing R¹, R¹, R², (CH₂)ₘ, S(O)ₙ substituents]

| Cmpd. No. | R¹ | R² | m | n | m.p. (°C.) |
|---|---|---|---|---|---|
| 1 (Ex. 1) | CH₃ | CH₃ | 1 | 2 | 60 (dec) |

Index TABLE B

[Structure: pyrazole-substituted analog with R¹, R¹, R², R⁵O, R⁶, R⁷, (CH₂)ₘ, S(O)ₙ]

| Cmpd. No. | R¹ | R² | R⁵ | R⁶ | R⁷ | m | n | m.p. (°C.) |
|---|---|---|---|---|---|---|---|---|
| 2 (Ex. 2) | CH₃ | CH₃ | H | CH₂CH₃ | H | 1 | 2 | 179–180 |
| 3 | CH₃ | Cl | H | CH₂CH₃ | H | 1 | 2 | >260 |

BIOLOGICAL EXAMPLES OF THE INVENTION

TEST A

Seeds of barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which included a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (-) response means no test result.

TABLE A

| | COMPOUND | | | COMPOUND | |
|---|---|---|---|---|---|
| Rate 2000 g/ha | 1 | 2 | Rate 2000 g/ha | 1 | 2 |
| POST-EMERGENCE | | | PRE-EMERGENCE | | |
| Barley | 1 | 8 | Barley | 0 | 3 |
| Barnyardgrass | 9 | 10 | Barnyardgrass | 6 | 8 |
| Bedstraw | 8 | 9 | Bedstraw | 9 | 9 |
| Blackgrass | 1 | 6 | Blackgrass | 0 | 1 |
| Chickweed | 8 | 10 | Chickweed | 3 | 9 |
| Cocklebur | 9 | 9 | Cocklebur | 9 | 8 |
| Corn | 0 | 4 | Corn | 0 | 0 |
| Cotton | 9 | 10 | Cotton | 8 | 3 |
| Crabgrass | 7 | 9 | Crabgrass | 9 | 10 |
| Downy brome | 0 | 1 | Downy brome | 1 | 0 |
| Giant foxtail | 6 | 9 | Giant foxtail | 4 | 9 |
| Lambsquarter | 9 | 10 | Lambsquarter | 10 | 9 |
| Morningglory | 9 | 2 | Morningglory | 9 | 1 |
| Nutsedge | 3 | 0 | Nutsedge | 10 | 0 |
| Rape | 9 | 10 | Rape | 9 | 10 |
| Rice | 9 | 9 | Rice | 9 | 9 |
| Sorghum | 3 | 9 | Sorghum | 1 | 6 |
| Soybean | 6 | 8 | Soybean | 6 | 6 |
| Sugar beet | 10 | 10 | Sugar beet | 10 | 10 |
| Velvetleaf | 10 | 9 | Velvetleaf | 10 | 8 |
| Wheat | 2 | 5 | Wheat | 0 | 3 |
| Wild buckwheat | 8 | 8 | Wild buckwheat | 7 | 2 |
| Wild oat | 3 | 7 | Wild oat | 1 | 4 |

| | COMPOUND | COMPOUND |
|---|---|---|
| Rate 200 g/ha | 3 | Rate 200 g/ha | 3 |
| POST-EMERGENCE | | PRE-EMERGENCE | |
| Barley | 1 | Barley | 0 |
| Barnyardgrass | 9 | Barnyardgrass | 0 |
| Bedstraw | 3 | Bedstraw | — |
| Blackgrass | 1 | Blackgrass | 1 |
| Chickweed | 8 | Chickweed | — |
| Cocklebur | 7 | Cocklebur | 0 |
| Corn | 1 | Corn | 0 |
| Cotton | 6 | Cotton | 0 |
| Crabgrass | 2 | Crabgrass | 2 |
| Downy brome | 0 | Downy brome | 0 |
| Giant foxtail | 4 | Giant foxtail | 0 |
| Lambsquarter | 9 | Lambsquarter | — |
| Morningglory | 6 | Morningglory | 6 |
| Nutsedge | 0 | Nutsedge | 4 |
| Rape | 4 | Rape | — |
| Rice | 6 | Rice | 0 |
| Sorghum | 4 | Sorghum | 0 |
| Soybean | 5 | Soybean | 0 |
| Sugar beet | 10 | Sugar beet | 8 |
| Velvetleaf | 2 | Velvetleaf | 6 |
| Wheat | 2 | Wheat | 0 |
| Wild buckwheat | 1 | Wild buckwheat | 0 |
| Wild oat | 2 | Wild oat | 0 |

| | COMPOUND | | | COMPOUND | |
|---|---|---|---|---|---|
| Rate 400 g/ha | 1 | 2 | Rate 400 g/ha | 1 | 2 |
| POST-EMERGENCE | | | PRE-EMERGENCE | | |
| Barley | 0 | 2 | Barley | 0 | 0 |
| Barnyardgrass | 9 | 9 | Barnyardgrass | 0 | 1 |
| Bedstraw | 7 | 8 | Bedstraw | 4 | 8 |
| Blackgrass | 1 | 1 | Blackgrass | 0 | 0 |
| Chickweed | 7 | 9 | Chickweed | 0 | 8 |
| Cocklebur | 9 | 9 | Cocklebur | 8 | 2 |
| Corn | 0 | 2 | Corn | 0 | 0 |

TABLE A-continued

| | | | | | |
|---|---|---|---|---|---|
| Cotton | 9 | 10 | Cotton | 4 | 0 |
| Crabgrass | 5 | 9 | Crabgrass | 8 | 8 |
| Downy brome | 0 | 0 | Downy brome | 0 | 0 |
| Giant foxtail | 3 | 9 | Giant foxtail | 0 | 7 |
| Lambsquarter | 9 | 9 | Lambsquarter | 9 | 9 |
| Morningglory | 9 | 0 | Morningglory | 6 | 0 |
| Nutsedge | 3 | 0 | Nutsedge | 2 | 0 |
| Rape | 9 | 9 | Rape | 5 | 0 |
| Rice | 8 | 9 | Rice | 0 | 0 |
| Sorghum | 3 | 7 | Sorghum | 0 | 0 |
| Soybean | 5 | 7 | Soybean | 0 | 1 |
| Sugar beet | 10 | 10 | Sugar beet | 10 | 10 |
| Velvetleaf | 10 | 8 | Velvetleaf | 9 | 3 |
| Wheat | 1 | 2 | Wheat | 0 | 0 |
| Wild buckwheat | 6 | 5 | Wild buckwheat | 1 | 0 |
| Wild oat | 2 | 6 | Wild oat | 0 | 0 |

| | COMPOUND | | | COMPOUND |
|---|---|---|---|---|
| Rate 50 g/ha | 3 | | Rate 50 g/ha | 3 |
| POST-EMERGENCE | | | PRE-EMERGENCE | |
| Barley | 0 | | Barley | 0 |
| Barnyardgrass | 8 | | Barnyardgrass | 0 |
| Bedstraw | 2 | | Bedstraw | 0 |
| Blackgrass | 1 | | Blackgrass | 0 |
| Chickweed | 7 | | Chickweed | — |
| Cocklebur | 6 | | Cocklebur | 0 |
| Corn | 2 | | Corn | 0 |
| Cotton | 7 | | Cotton | 0 |
| Crabgrass | 1 | | Crabgrass | 0 |
| Downy brome | 0 | | Downy brome | 0 |
| Giant foxtail | 1 | | Giant foxtail | 0 |
| Lambsquarter | 8 | | Lambsquarter | — |
| Morningglory | 3 | | Morningglory | 0 |
| Nutsedge | 0 | | Nutsedge | 0 |
| Rape | 2 | | Rape | — |
| Rice | 5 | | Rice | 0 |
| Sorghum | 2 | | Sorghum | 0 |
| Soybean | 4 | | Soybean | 0 |
| Sugar beet | 7 | | Sugar beet | 0 |
| Velvetleaf | 2 | | Velvetleaf | 0 |
| Wheat | 1 | | Wheat | 0 |
| Wild buckwheat | 1 | | Wild buckwheat | — |
| Wild oat | 2 | | Wild oat | 0 |

TEST B

The compounds evaluated in this test were formulated in a non-phytotoxic solvent mixture which included a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), johnsongrass (*Sorghum halepense*), lambsquarters (*Chenopodium album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and late watergrass (*Echinochloa oryzicola*) grown to the 2 leaf (2 L) stage for testing.

All plant species were grown using normal greenhouse practices. Visual evaluations of injury expressed on treated plants, when compared to untreated controls, were recorded approximately fourteen to twenty one days after application of the test compound. Plant response to the test compound are summarized in Table B, recorded on a 0 to 100 scale where 0 is no effect and 100 is complete control. A dash (-) response means no test result.

TABLE B

| | COMPOUND | | | COMPOUND | |
|---|---|---|---|---|---|
| Rate 500 g/ha | 1 | 2 | Rate 500 g/ha | 1 | 2 |
| POST-EMERGENCE | | | PRE-EMERGENCE | | |
| Barley Igri | 0 | 25 | Barley Igri | 0 | 0 |
| Barnyard, 2 L | 40 | 85 | Barnyardgrass | 70 | 70 |
| Barnyardgrass | 90 | 95 | Bedstraw | 0 | 40 |
| Bedstraw | 20 | 80 | Blackgrass | 10 | 0 |
| Blackgrass | 0 | 30 | Chickweed | — | 100 |
| Chickweed | 95 | 95 | Cocklebur | 85 | 30 |
| Cocklebur | 90 | 90 | Corn | 0 | 0 |
| Corn | 40 | 35 | Cotton | 75 | 0 |
| Cotton | 100 | 100 | Crabgrass | 40 | 100 |
| Crabgrass | 50 | 90 | Downy Brome | 0 | 0 |
| Downy Brome | 0 | 0 | Giant foxtail | 75 | 95 |
| Duck salad | 70 | 90 | Italn. Ryegrass | 0 | 0 |
| Giant foxtail | 65 | 90 | Johnsongrass | 0 | 40 |
| Italn. Ryegrass | 0 | 20 | Lambsquarter | 100 | 100 |
| Johnsongrass | 20 | 90 | Morningglory | 40 | 70 |
| Lambsquarter | 95 | 100 | Rape | 95 | 30 |
| Morningglory | — | 90 | Redroot Pigweed | 10 | 10 |
| Rape | 100 | 100 | Soybean | 40 | 20 |
| Redroot Pigweed | 20 | 85 | Speedwell | 90 | 70 |
| Rice Japonica | 45 | 85 | Sugar beet | 100 | 100 |
| Soybean | 80 | 90 | Velvetleaf | 85 | 50 |
| Speedwell | 70 | 50 | Wheat | 0 | 0 |
| Sugar beet | 100 | 100 | Wild buckwheat | 10 | 20 |
| Umbrella sedge | 80 | 75 | Wild oat | 0 | 0 |
| Velvetleaf | 90 | 85 | | | |
| Watergrass, 2 L | 10 | 60 | | | |
| Wheat | 0 | 25 | | | |
| Wild buckwheat | 30 | 40 | | | |
| Wild oat | 20 | 35 | | | |

| | COMPOUND | | | COMPOUND | |
|---|---|---|---|---|---|
| Rate 250 g/ha | 1 | 2 | Rate 250 g/ha | 1 | 2 |
| POST-EMERGENCE | | | PRE-EMERGENCE | | |
| Barley Igri | 0 | 20 | Barley Igri | 0 | 0 |
| Barnyard, 2 L | 25 | 70 | Barnyardgrass | 35 | 60 |
| Barnyardgrass | 80 | 95 | Bedstraw | 0 | 40 |
| Bedstraw | 20 | 60 | Blackgrass | 10 | 0 |
| Blackgrass | 0 | 10 | Chickweed | 95 | 90 |
| Chickweed | 90 | 95 | Cocklebur | 70 | 20 |
| Cocklebur | 90 | 90 | Corn | 0 | 0 |

TABLE B-continued

| | | | | | |
|---|---|---|---|---|---|
| Corn | 10 | 25 | Cotton | 50 | 0 |
| Cotton | 100 | 90 | Crabgrass | 30 | 95 |
| Crabgrass | 35 | 80 | Downy Brome | 0 | 0 |
| Downy Brome | 0 | 0 | Giant foxtail | 0 | 95 |
| Duck salad | 40 | 80 | Italn. Rygrass | 0 | 0 |
| Giant foxtail | 35 | 90 | Johnsongrass | 0 | 40 |
| Italn. Rygrass | 0 | 10 | Lambsquarter | 95 | 95 |
| Johnsongrass | 10 | 80 | Morningglory | 40 | 20 |
| Lambsquarter | 95 | 100 | Rape | 70 | 0 |
| Morningglory | — | 90 | Redroot Pigweed | 0 | 0 |
| Rape | 100 | 100 | Soybean | 20 | 0 |
| Redroot Pigweed | 15 | 85 | Speedwell | 0 | 30 |
| Rice Japonica | 40 | 80 | Sugar beet | 100 | 100 |
| Soybean | 50 | 75 | Velvetleaf | 70 | 30 |
| Speedwell | 50 | 35 | Wheat | 0 | 0 |
| Sugar beet | 100 | 100 | Wild buckwheat | 10 | 0 |
| Umbrella sedge | 40 | 75 | Wild oat | 0 | 0 |
| Velvetleaf | 80 | 75 | | | |
| Watergrass, 2 L | 10 | 60 | | | |
| Wheat | 0 | 0 | | | |
| Wild buckwheat | 0 | 40 | | | |
| Wild oat | 20 | 30 | | | |

| | COMPOUND | | | COMPOUND | |
|---|---|---|---|---|---|
| Rate 125 g/ha | 1 | 2 | Rate 125 g/ha | 1 | 2 |
| POSTEMERGENCE | | | PREEMERGENCE | | |
| Barley Igri | 0 | 0 | Barley Igri | 0 | 0 |
| Barnyard, 2 L | 0 | 30 | Barnyardgrass | 20 | 10 |
| Barnyardgrass | 50 | 90 | Bedstraw | 0 | 40 |
| Bedstraw | 0 | 10 | Blackgrass | 10 | 0 |
| Blackgrass | 0 | 0 | Chickweed | 0 | 40 |
| Chickweed | 50 | 95 | Cocklebur | 40 | 0 |
| Cocklebur | 90 | 80 | Corn | 0 | 0 |
| Corn | 0 | 20 | Cotton | 30 | 0 |
| Cotton | 100 | 90 | Crabgrass | 20 | 75 |
| Crabgrass | 30 | 70 | Downy Brome | 0 | 0 |
| Downy Brome | 0 | 0 | Giant foxtail | 0 | 60 |
| Duck salad | 20 | 60 | Italn. Rygrass | 0 | 0 |
| Giant foxtail | 25 | 90 | Johnsongrass | 0 | 20 |
| Italn. Rygrass | 0 | 0 | Lambsquarter | 95 | 95 |
| Johnsongrass | — | 70 | Morningglory | 30 | 0 |
| Lambsquarter | 70 | 100 | Rape | 30 | 0 |
| Morningglory | — | 90 | Redroot Pigweed | 0 | 0 |
| Rape | 85 | 95 | Soybean | 0 | 0 |
| Redroot Pigweed | 10 | 70 | Speedwell | 0 | 0 |
| Rice Japonica | 0 | 75 | Sugar beet | 90 | 100 |
| Soybean | 40 | 65 | Velvetleaf | 55 | 10 |
| Speedwell | 50 | 25 | Wheat | 0 | 0 |
| Sugar beet | 100 | 100 | Wild buckwheat | 0 | 0 |
| Umbrella sedge | 20 | 50 | Wild oat | 0 | 0 |
| Velvetleaf | 75 | 70 | | | |
| Watergrass, 2 L | 10 | 30 | | | |
| Wheat | 0 | 0 | | | |
| Wild buckwheat | 0 | 35 | | | |
| Wild oat | 20 | 10 | | | |

| | COMPOUND | | | COMPOUND | |
|---|---|---|---|---|---|
| Rate 62 g/ha | 1 | 2 | Rate 62 g/ha | 1 | 2 |
| POSTEMERGENCE | | | PREEMERGENCE | | |
| Barley Igri | 0 | 0 | Barley Igri | 0 | 0 |
| Barnyard, 2 L | 0 | 25 | Barnyardgrass | 0 | 0 |
| Barnyardgrass | 35 | 75 | Bedstraw | 0 | 0 |
| Bedstraw | 0 | 10 | Blackgrass | 10 | 0 |
| Blackgrass | 0 | 0 | Chickweed | 0 | 10 |
| Chickweed | 10 | 95 | Cocklebur | — | 0 |
| Cocklebur | 80 | 50 | Corn | 0 | 0 |
| Corn | 0 | 15 | Cotton | 20 | 0 |
| Cotton | 90 | 90 | Crabgrass | 10 | 35 |
| Crabgrass | 25 | 50 | Downy Brome | 0 | 0 |

TABLE B-continued

| | | | | | |
|---|---|---|---|---|---|
| Downy Brome | 0 | 0 | Giant foxtail | 0 | 40 |
| Duck salad | 10 | 20 | Italn. Rygrass | 0 | 0 |
| Giant foxtail | 20 | 85 | Johnsongrass | 0 | 15 |
| Italn. Rygrass | 0 | 0 | Lambsquarter | 85 | 95 |
| Johnsongrass | — | 60 | Morningglory | 10 | 0 |
| Lambsquarter | 40 | 100 | Rape | 0 | 0 |
| Morningglory | — | 85 | Redroot Pigweed | 0 | 0 |
| Rape | 85 | 95 | Soybean | 0 | 0 |
| Redroot Pigweed | 0 | 35 | Speedwell | 0 | 0 |
| Rice Japonica | 0 | 40 | Sugar beet | 70 | 0 |
| Soybean | 20 | 65 | Velvetleaf | 0 | 0 |
| Speedwell | 50 | 25 | Wheat | 0 | 0 |
| Sugar beet | 90 | 95 | Wild buckwheat | 0 | 0 |
| Umbrella sedge | 20 | 40 | Wild oat | 0 | 0 |
| Velvetleaf | 55 | — | | | |
| Watergrass, 2 L | 10 | 20 | | | |
| Wheat | 0 | 0 | | | |
| Wild buckwheat | 0 | 35 | | | |
| Wild oat | 10 | 10 | | | |

TEST C

Compounds evaluated in this test were formulated in a non-phytotoxic solvent mixture which included a surfactant, applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include annual bluegrass (*Poa annua*), black nightshade (*Solanum nigra*), blackgrass (*Alopecurus myosuroides*), chickweed (*Stellaria media*), deadnettle (*Lamium amplexicaule*), downy brome (*Bromus tectorum*), field violet (*Viola arvensis*), galium (*Gatium aparine*), green foxtail (*Setaria viridis*), jointed goatgrass (*Aegilops cylindrica*), kochia (*Kochia scoparia*), lambsquarters (*Chenopodium album*), littleseed canarygrass (*Phalaris minor*), rape (*Brassica napus*), redroot pigweed (*Amaranthus retroflexus*), ryegrass (*Lolium multifiorum*), scentless chamomile (*Matricaria inodora*), speedwell (*Veronica persica*), spring barely (*Hordeum vutgare* cv. 'Klages'), spring wheat (*Triticum aestivum* cv. 'ERA'), sugar beet (*Beta vulgaris* cv. 'US1'), sunflower (*Helianthus annuus* cv. 'Russian Giant'), wild buckwheat (*Polygonum convolvulus*), wild mustard (*Sinapis arvensis*), wild oat (*Avena fatua*), windgrass (*Apera spica-venti*), winter barley (*Hordeum vutgare* cv. 'Igri') and winter wheat (*Triticum aestivum* cv. 'Talent').

Treated plants and untreated controls were maintained in a greenhouse for approximately 21 to 28 days, after which all treated plants were compared to untreated controls and visually evaluated. Plant response ratings, summarized in Table C, are based upon a 0 to 100 scale where 0 is no effect and 100 is complete control. A dash response (-) means no test result.

TABLE C

| Rate 125 g/ha | COMPOUND 1 | Rate 62 g/ha | COMPOUND 1 | COMPOUND 2 |
|---|---|---|---|---|
| POST-EMERGENCE | | POST-EMERGENCE | | |
| Blk Nightshade | 80 | Blk Nightshade | 75 | 75 |
| Chickweed | 100 | Chickweed | 70 | 65 |
| Deadnettle | 75 | Deadnettle | 60 | 40 |
| Field violet | 60 | Field violet | 50 | 60 |
| Galium | 55 | Galium | 40 | 55 |
| Kochia | 25 | Kochia | 35 | 80 |
| Lambsquarters | 100 | Lambsquarters | 100 | 100 |
| Rape | 70 | Rape | 60 | 60 |
| Redroot Pigweed | 20 | Redroot Pigweed | 20 | 70 |
| Scentless Chamo | 65 | Scentless Chamo | 55 | 65 |
| Speedwell | 70 | Speedwell | 60 | 50 |
| Spring Barley | 0 | Spring Barley | 0 | 0 |
| Sugar beet | 100 | Sugar beet | 80 | 100 |
| Sunflower | 60 | Sunflower | 40 | 70 |
| Wheat (Spring) | 15 | Wheat (Spring) | 5 | 5 |
| Wheat (Winter) | 5 | Wheat (Winter) | 0 | 0 |
| Wild buckwheat | 45 | Wild buckwheat | 60 | 45 |
| Winter Barley | 10 | Winter Barley | 10 | 10 |

| Rate 31 g/ha | COMPOUND 2 |
|---|---|
| POST-EMERGENCE | |
| Blk Nightshade | 75 |
| Chickweed | 50 |
| Deadnettle | 40 |
| Field violet | 55 |
| Galium | 50 |
| Kochia | 60 |
| Lambsquarters | 100 |
| Rape | 45 |
| Redroot Pigweed | — |
| Scentless Chamo | 70 |
| Speedwell | 65 |
| Spring Barley | 0 |
| Sugar beet | 100 |
| Sunflower | 60 |
| Wheat (Spring) | 5 |
| Wheat (Winter) | 0 |
| Wild buckwheat | 55 |
| Winter Barley | 0 |

What is claimed is:

1. A compound selected from Formula I and agriculturally suitable salts thereof,

I wherein

Q is

Q-1 or

Q-2 each $R^1$ is independently $C_1$–$C_6$ alkyl, $C_1$–$C_6$ haloalkyl, $C_1$–$C_6$ alkoxy, $C_1$–$C_6$ haloalkoxy, hydroxy, or halogen; or two $R^1$ bonded to the same carbon atom can be taken together with the carbon to which they are attached to form C(=O) or C(=N—$OR^8$); or two $R^1$ bonded to the same carbon atom can be taken together as —$OCH_2CH_2O$— or —$OCH_2CH_2CH_2O$—, each optionally substituted with 1–2 $C_1$—$C_3$ alkyl or 1–4 halogen;

$R^2$ is H, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl, halogen, cyano or nitro;

$R^3$ is $OR^9$, $C_1$–$C_6$ alkylthio, $C_1$–$C_6$ haloalkylthio, $C_1$–$C_6$ alkylsulfinyl, $C_1$–$C_6$ haloalkylsulfinyl, $C_1$–$C_6$ alkylsulfonyl, $C_1$–$C_6$ haloalkylsulfonyl or halogen;

each $R^4$ is independently $C_1$–$C_3$ alkyl, $C_1$–$C_3$ alkoxy, $C_1$–$C_3$ alkylthio or halogen; or when two $R^4$ are attached to the same carbon atom, then said $R^4$ pair can be taken together to form —$OCH_2CH_2O$—, —$OCH_2CH_2CH_2O$—, —$SCH_2CH_2S$— or —$SCH_2CH_2CH_2S$—, each group optionally substituted with 1–4 $CH_3$;

$R^5$ is H, $C_1$–$C_6$ alkyl, $C_1$–$C_6$ haloalkyl, $C_2$–$C_6$ alkoxyalkyl, formyl, $C_2$–$C_6$ alkylcarbonyl, $C_2$–$C_6$ alkoxycarbonyl, $C_2$–$C_6$ alkylaminocarbonyl, $C_3$–$C_7$ dialkylaminocarbonyl, $C_1$–$C_6$ alkylsulfonyl or $C_1$–$C_6$ haloalkylsulfonyl; or $R^5$ is benzoyl or phenylsulfonyl, each optionally substituted with $C_1$–$C_3$ alkyl, halogen, cyano or nitro;

$R^6$ is H, $C_1$–$C_6$ alkyl, $C_1$–$C_6$ haloalkyl, $C_3$–$C_6$ alkenyl or $C_3$–$C_6$ alkynyl; or $R^6$ is phenyl or benzyl, each optionally substituted on the phenyl ring with $C_1$–$C_3$ alkyl, halogen, cyano or nitro;

$R^7$ is H, $C_1$–$C_6$ alkyl, $C_1$–$C_6$ haloalkyl, halogen, cyano, or nitro;

$R^8$ is H, $C_1$–$C_6$ alkyl, $C_1$–$C_6$ haloalkyl, C3-$C_6$ alkenyl or $C_3$–$C_6$ alkynyl;

$R^9$ is H, $C_1$–$C_6$ alkyl, $C_1$–$C_6$ haloalkyl, C2-$C_6$ alkoxyalkyl, formyl, $C_2$–$C_6$ alkylcarbonyl, $C_2$–$C_6$ alkoxycarbonyl, $C_2$–$C_6$ alkylaminocarbonyl, $C_3$–$C_7$ dialkylaminocarbonyl, $C_1$–$C_6$ alkylsulfonyl or $C_1$–$C_6$ haloalkylsulfonyl; or $R^9$ is benzoyl or phenylsulfonyl, each optionally substituted with $C_1$–$C_3$ alkyl, halogen, cyano or nitro;

m is 1 or 2;

n is 0, 1 or 2; and p and q are each independently 0, 1, 2, 3 or 4; provided that, when Q is Q-1, then n is 1 or 2.

2. A compound of claim 1 wherein:

$R^2$ is $C_1$–$C_3$ alkyl or halogen;

$R^4$ is $C_1$–$C_3$ alkyl;

$R^6$ is H, $C_1$–$C_6$ alkyl or $C_3$–$C_6$ alkenyl;

$R^7$ is H;

$R^9$ is H, formyl, $C_2-C_6$ alkylcarbonyl, $C_2-C_6$ alkoxycarbonyl, $C_2-C_6$ alkylaminocarbonyl, $C_3-C_7$ dialkylaminocarbonyl, $C_1-C_6$ alkylsulfonyl or $C_1-C_6$ haloalkylsulfonyl; or $R^9$ is benzoyl or phenylsulfonyl, each optionally substituted with $C_1-C_3$ alkyl, halogen, cyano or nitro; and n is 2.

3. A compound of claim 2 wherein:

each $R^1$ is independently $C_1-C_3$ alkyl, $C_1-C_3$ alkoxy or halogen; or two $R^1$ bonded to the same carbon atom can be taken together with the carbon to which they are attached to form C(=O) or C(=N—$OR^8$); or two $R^1$ bonded to the same carbon atom can be taken together as —OCH$_2$CH$_2$O— or —OCH$_2$CH$_2$CH$_2$O—, each optionally substituted with 1–2 $C_1-C_3$ alkyl or 1–4 halogen;

$R^2$ is methyl or halogen;

$R^3$ is $OR^9$;

$R^5$ is H or $C_1-C_2$ alkylsulfonyl; or $R^5$ is benzoyl or phenylsulfonyl, each optionally substituted with $C_1-C_3$ alkyl, halogen, cyano or nitro;

$R^8$ is $C_1-C_3$ alkyl;

$R^9$ is H or $C_1-C_2$ alkylsulfonyl; or $R^9$ is benzoyl or phenylsulfonyl, each optionally substituted with $C_1-C_3$ alkyl, halogen, cyano or nitro; and m is 1.

4. The compounds of claim 3 which are selected from the group:

2-[(5,6-dihydro-3,4,4-trimethyl-4H-thieno[2,3-b]thiopyran-2-yl)carbonyl]-1,3-cyclohexanedione S,S-dioxide;

(5,6-dihydro-3,4,4-trimethyl-4H-thieno[2,3-b]thiopyran-2-yl)(1-ethyl-5-hydroxy-1H-pyrazol-4-yl)methanone S,S-dioxide;

2-[(5,6-dihydro-3-methylspiro[1,3-dioxolane-2,4'-[4H]thieno[2,3-b]thiopyran]-2-yl)carbonyl]-1,3-cyclohexanedione S,S-dioxide; and (5,6-dihydro-3-methylspiro[1,3-dioxolane-2,4'-[4H]thieno[2,3-b]thiopyran]-2-yl)(1-ethyl-5-hydroxy-1H-pyrazol-4-yl)methanone S,S-dioxide.

5. A herbicidal composition comprising a herbicidally effective amount of a compound of claim 1 and at least one of a surfactant, a solid diluent or a liquid diluent.

6. A method for controlling the growth of undesired vegetation comprising contacting the vegetation or its environment with a herbicidally effective amount of a compound of claim 1.

* * * * *